United States Patent
Ray et al.

(10) Patent No.: US 6,350,252 B2
(45) Date of Patent: *Feb. 26, 2002

(54) METHODS AND DEVICES FOR OCCLUDING THE ASCENDING AORTA AND MAINTAINING CIRCULATION OF OXYGENATED BLOOD IN THE PATIENT WHEN THE PATIENT'S HEART IS ARRESTED

(75) Inventors: Pinaki Ray, Fremont; William W. Malecki, San Francisco; Jan Komtebedde, Cupertino, all of CA (US)

(73) Assignee: Heartport, Inc., Redwood City, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/112,514

(22) Filed: Jul. 9, 1998

Related U.S. Application Data

(63) Continuation-in-part of application No. 09/012,833, filed on Jan. 23, 1998, now Pat. No. 6,159,178.

(51) Int. Cl.$^7$ ............................................. A61M 29/00
(52) U.S. Cl. ...................................... 604/107; 604/105
(58) Field of Search .......................... 604/96, 104–109; 606/191, 194, 198

(56) References Cited

U.S. PATENT DOCUMENTS

| | | |
|---|---|---|
| 504,424 A | 9/1893 | Pezzer |
| 1,271,456 A * | 7/1918 | Flack ......................... 604/104 |
| 3,108,595 A | 10/1963 | Overment |
| 3,334,629 A * | 8/1967 | Cohn |
| 3,397,699 A | 8/1968 | Kohl |
| 3,557,794 A | 1/1971 | VanPatten |
| 3,568,659 A | 3/1971 | Karnegis |
| 3,799,172 A | 3/1974 | Szpur |
| 3,837,347 A | 9/1974 | Tower |
| 4,585,000 A | 4/1986 | Hershenson |
| 5,112,347 A | 5/1992 | Taheri |
| 5,188,630 A * | 2/1993 | Christoudias ................ 606/1 |
| 5,197,971 A | 3/1993 | Bonutti |
| 5,409,460 A | 4/1995 | Krumme |
| 5,456,667 A | 10/1995 | Ham et al. |
| 5,527,282 A * | 6/1996 | Segal ......................... 604/104 |
| 5,545,214 A * | 8/1996 | Stevens ........................ 623/2 |
| 5,700,242 A | 12/1997 | Mulder |
| 5,702,365 A | 12/1997 | King |
| 5,702,410 A * | 12/1997 | Klunder et al. ............. 606/194 |
| 5,725,552 A | 3/1998 | Kotula et al. |
| 5,827,237 A | 10/1998 | Macoviak et al. |
| 5,865,802 A * | 2/1999 | Yoon et al. ................. 604/104 |
| 5,868,708 A * | 2/1999 | Hart et al. .................. 604/104 |
| 5,916,193 A * | 6/1999 | Stevens et al. ............... 604/53 |
| 5,928,260 A * | 7/1999 | Chin et al. .................. 606/200 |

FOREIGN PATENT DOCUMENTS

| WO | WO 97/48436 | 12/1997 |
|---|---|---|

* cited by examiner

*Primary Examiner*—Sharon Kennedy
(74) *Attorney, Agent, or Firm*—Hoekendijk & Lynch, LLP.

(57) ABSTRACT

A device and method for occluding a patient's ascending aorta, maintaining circulation of oxygenated blood in the patient and delivering cardioplegic fluid to arrest the patient's heart. An aortic occlusion device has an occluding member in the form of a non-inflatable structure which is moved mechanically between collapsed and expanded orientations. The device is introduced into the ascending aorta in its collapsed orientation and is moved to its expanded orientation to occlude the aorta. The aortic occlusion includes a lumen through which blood is delivered to the patient. The lumen may be provided in the aortic occlusion device or in a separate cannula coupled to the device.

19 Claims, 26 Drawing Sheets

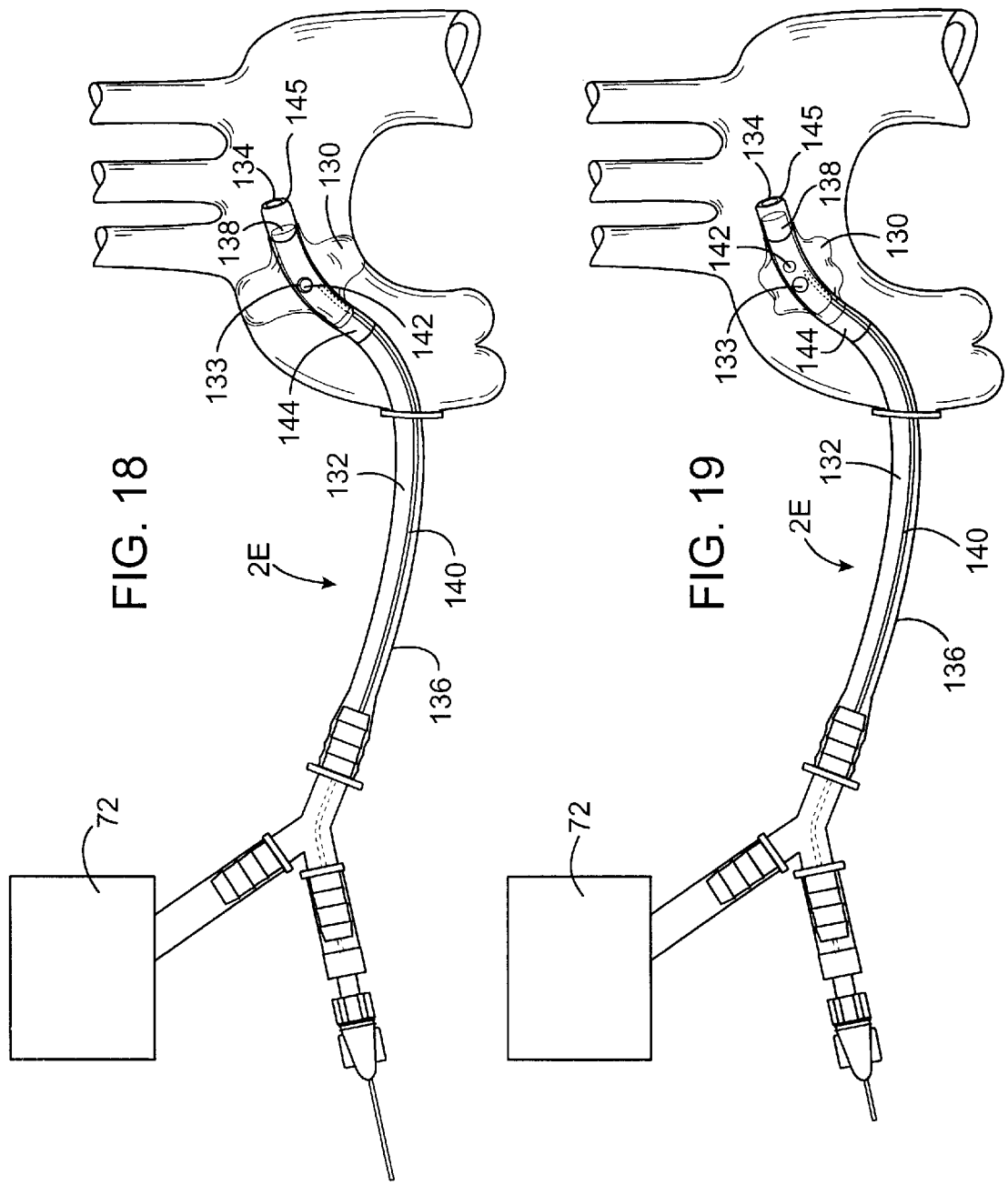

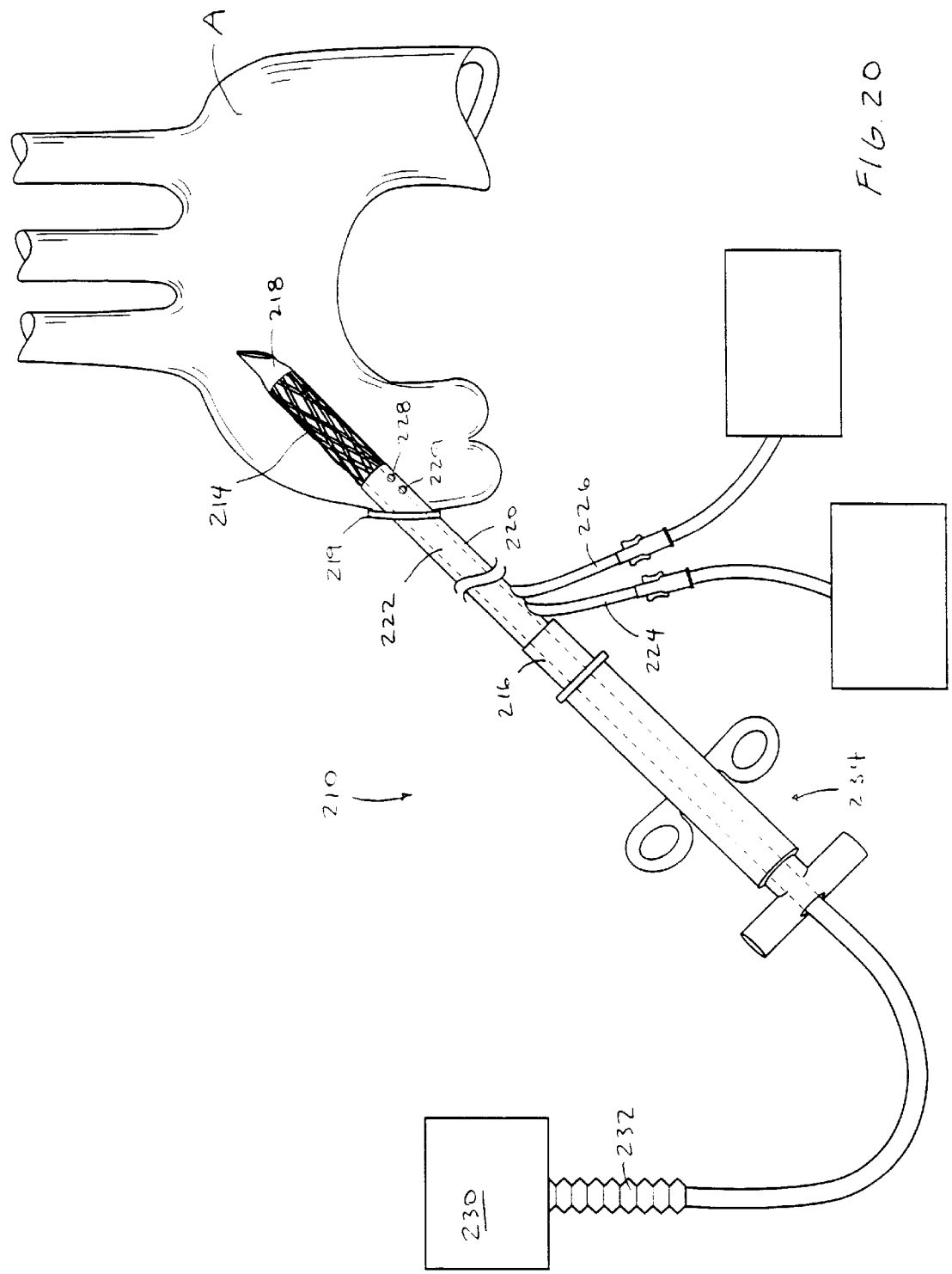

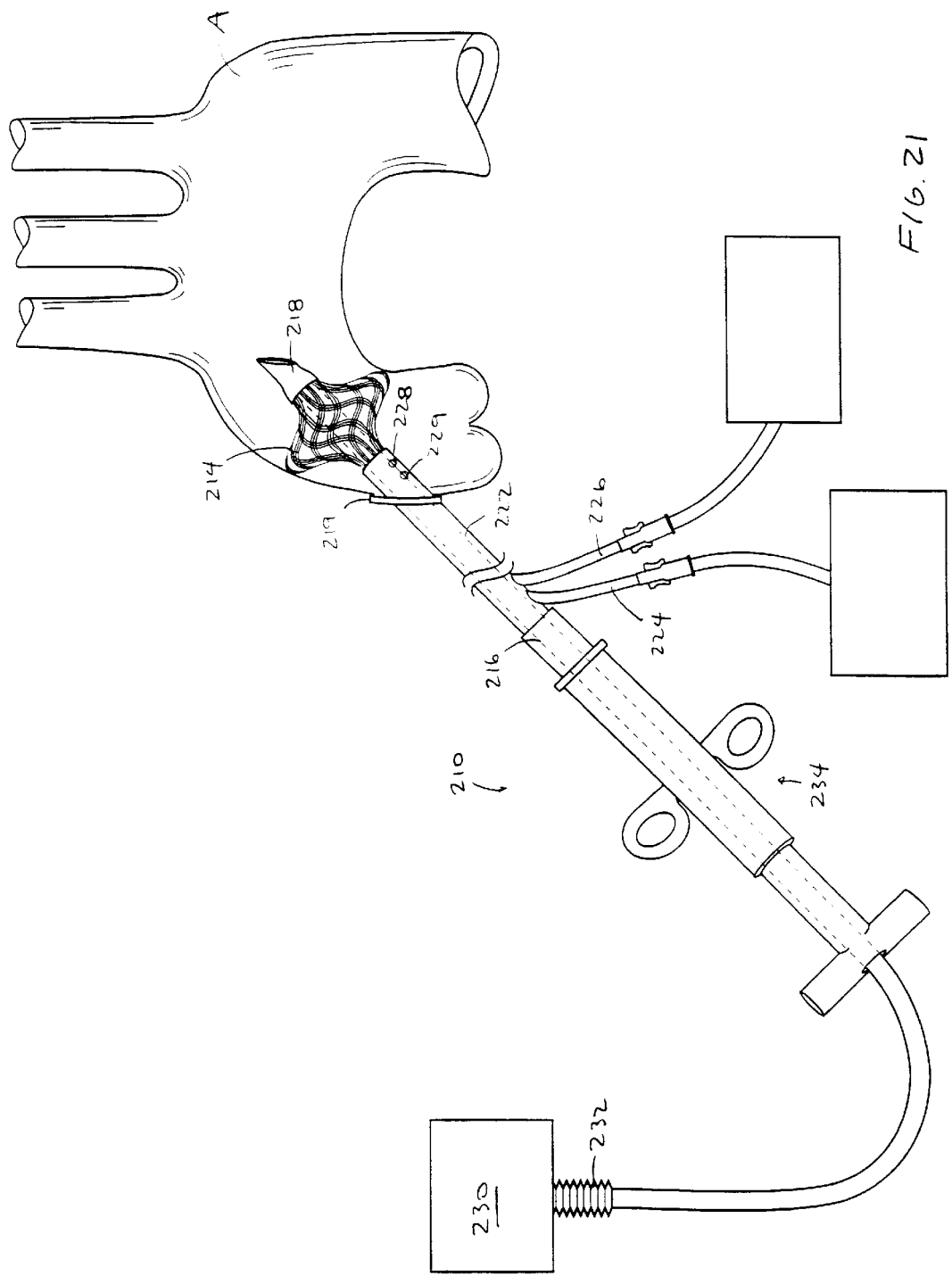

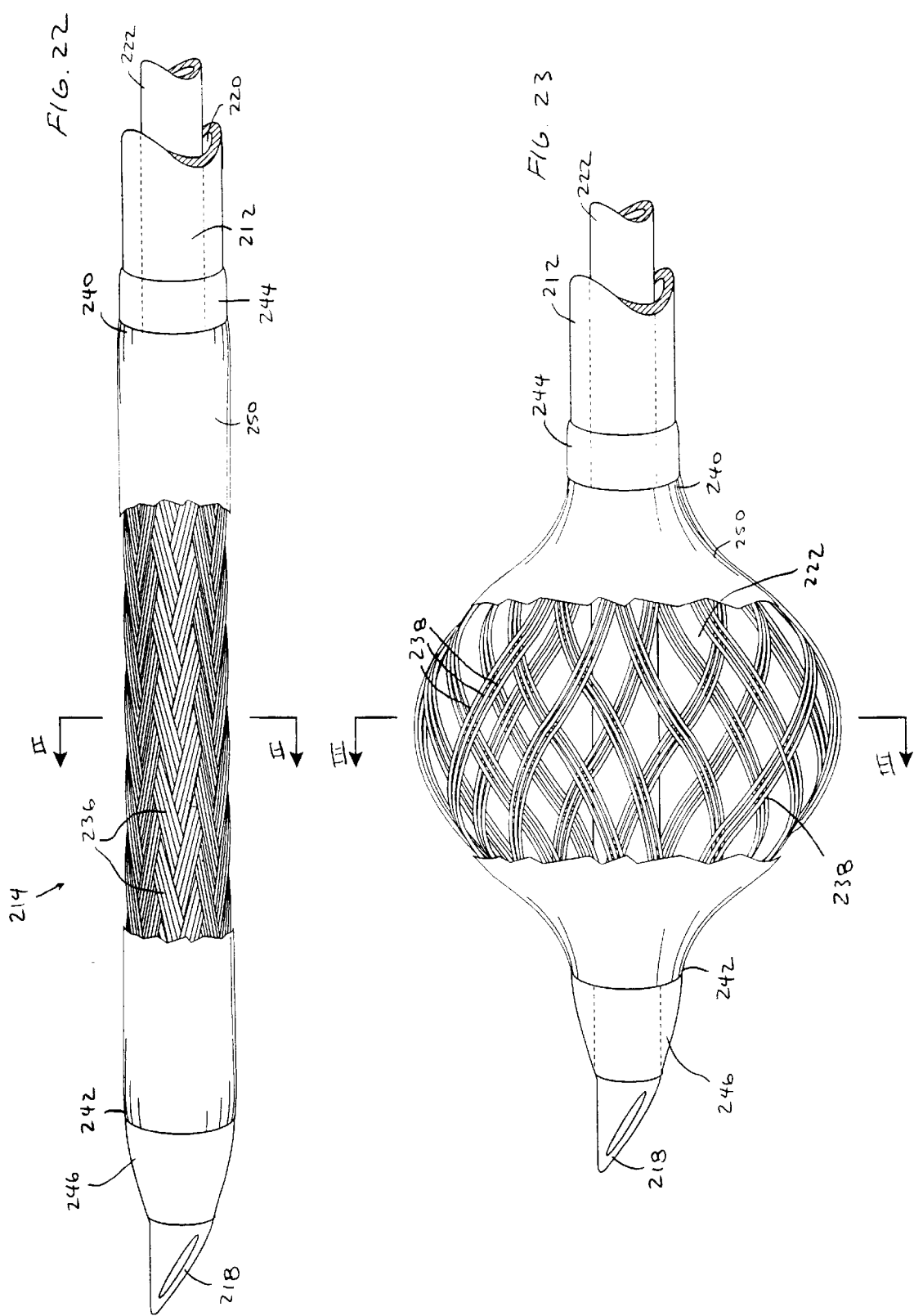

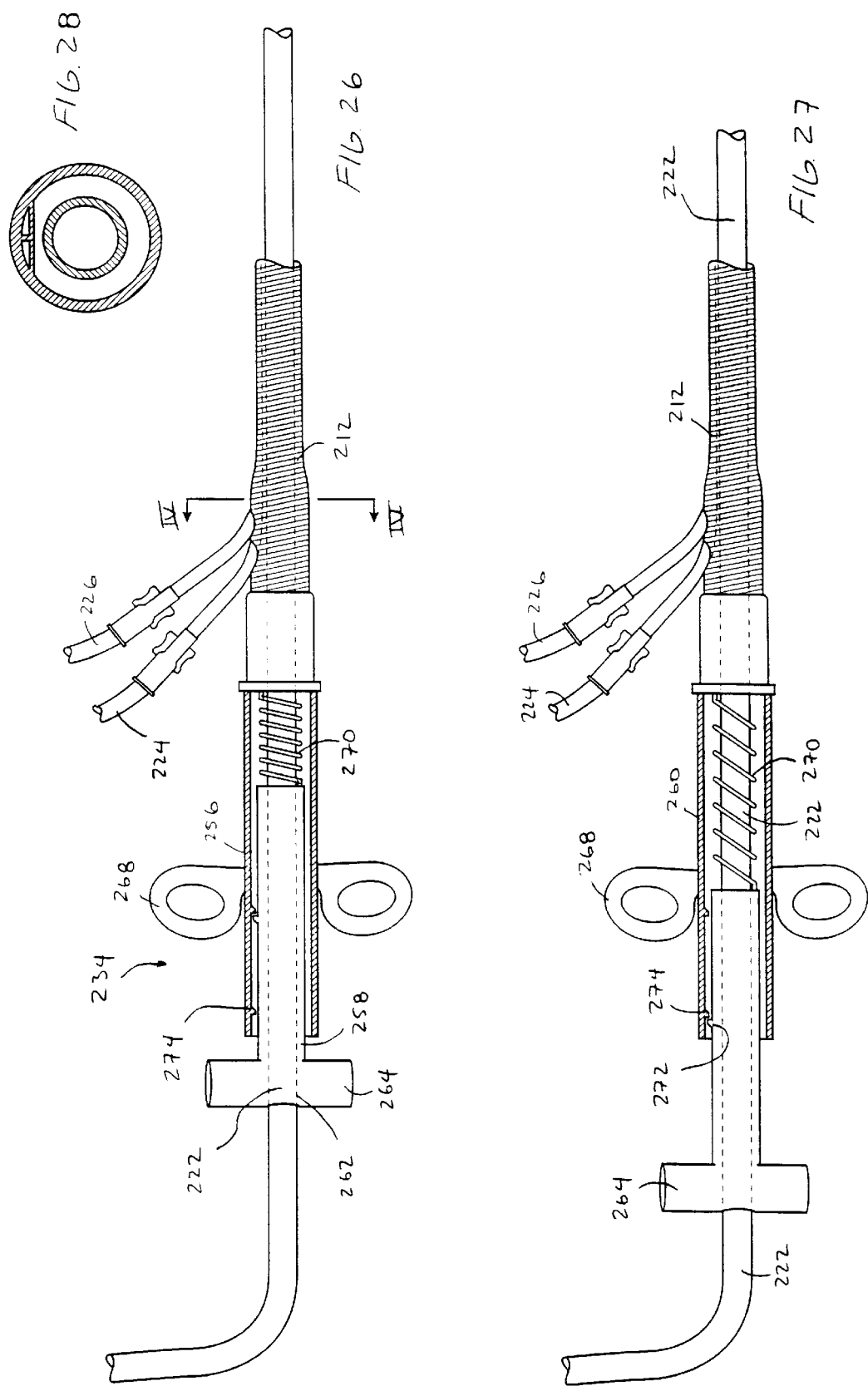

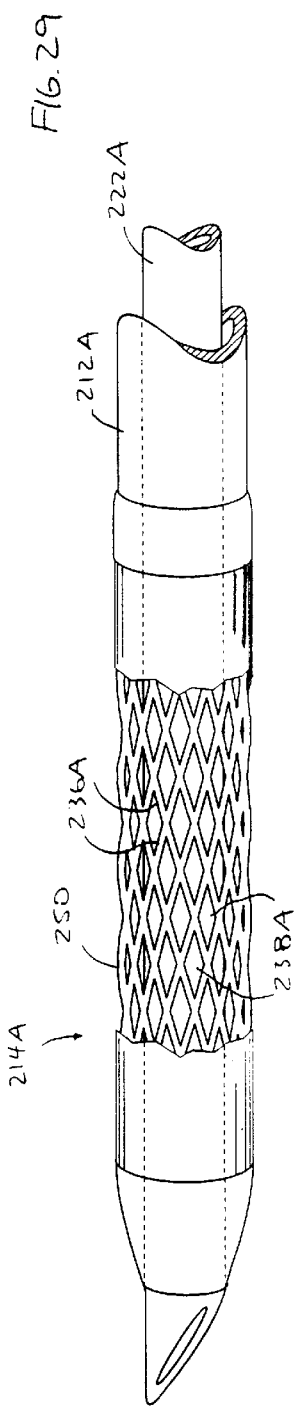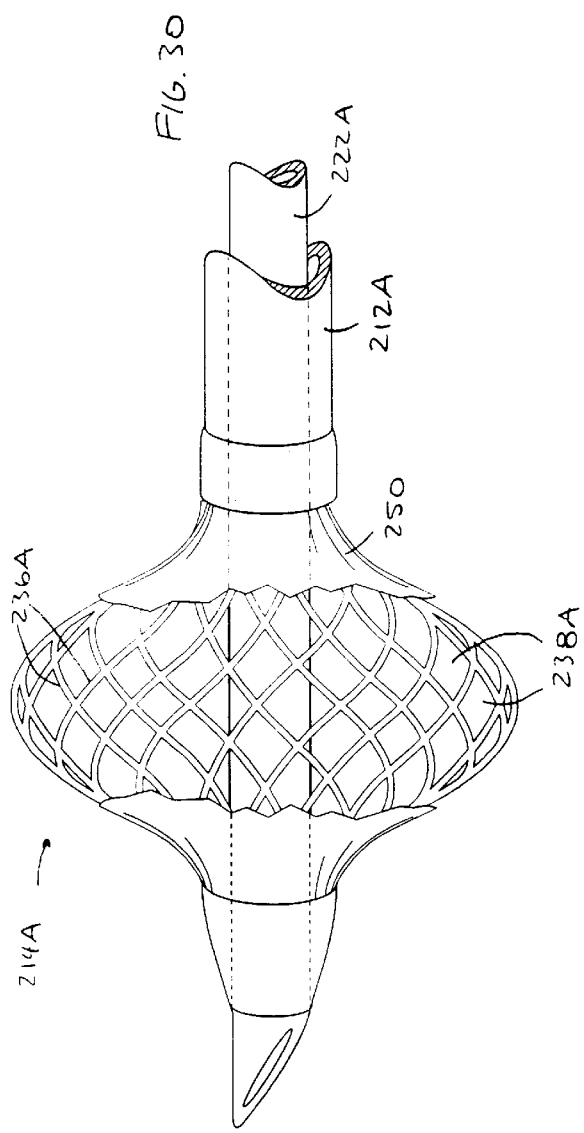

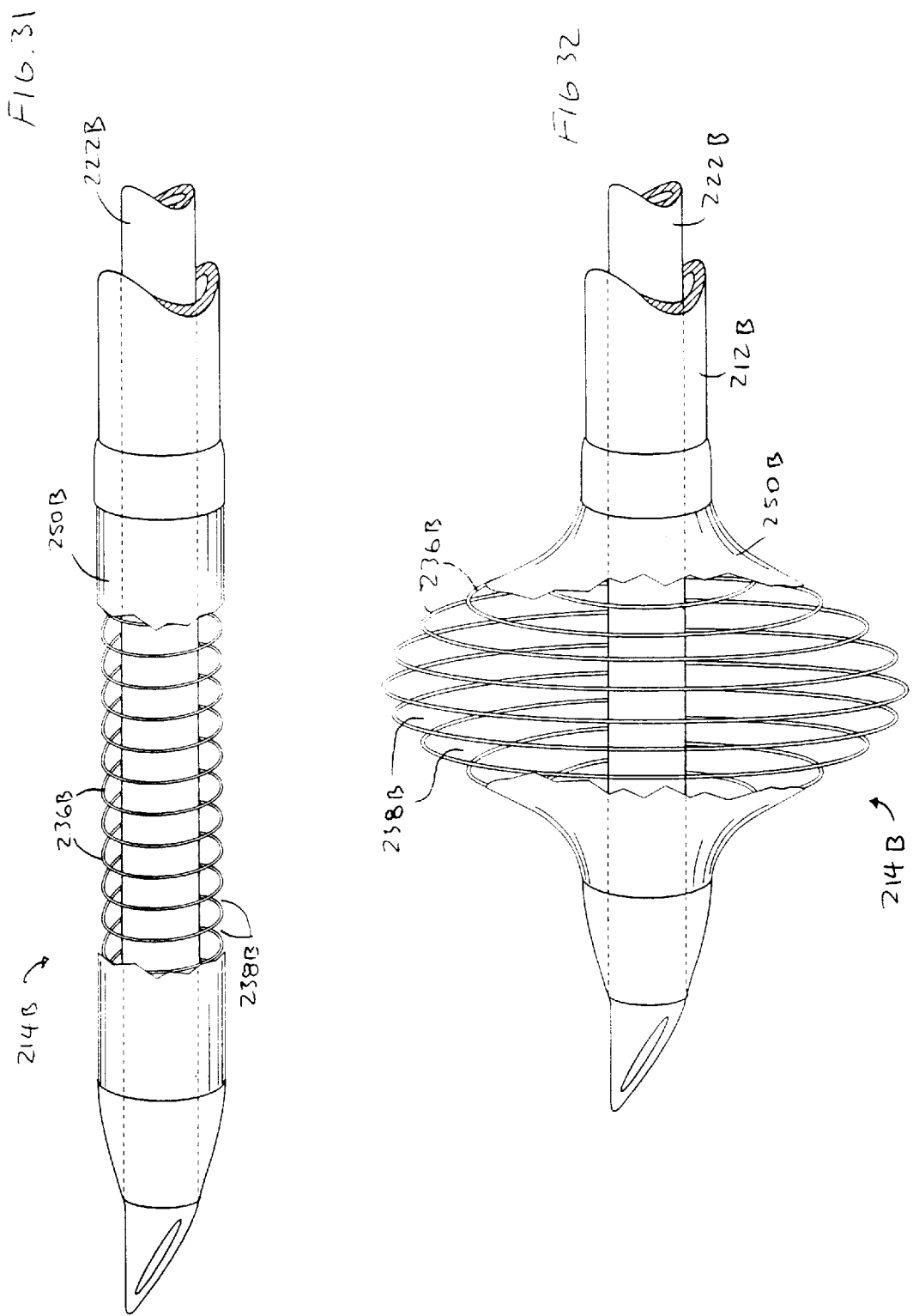

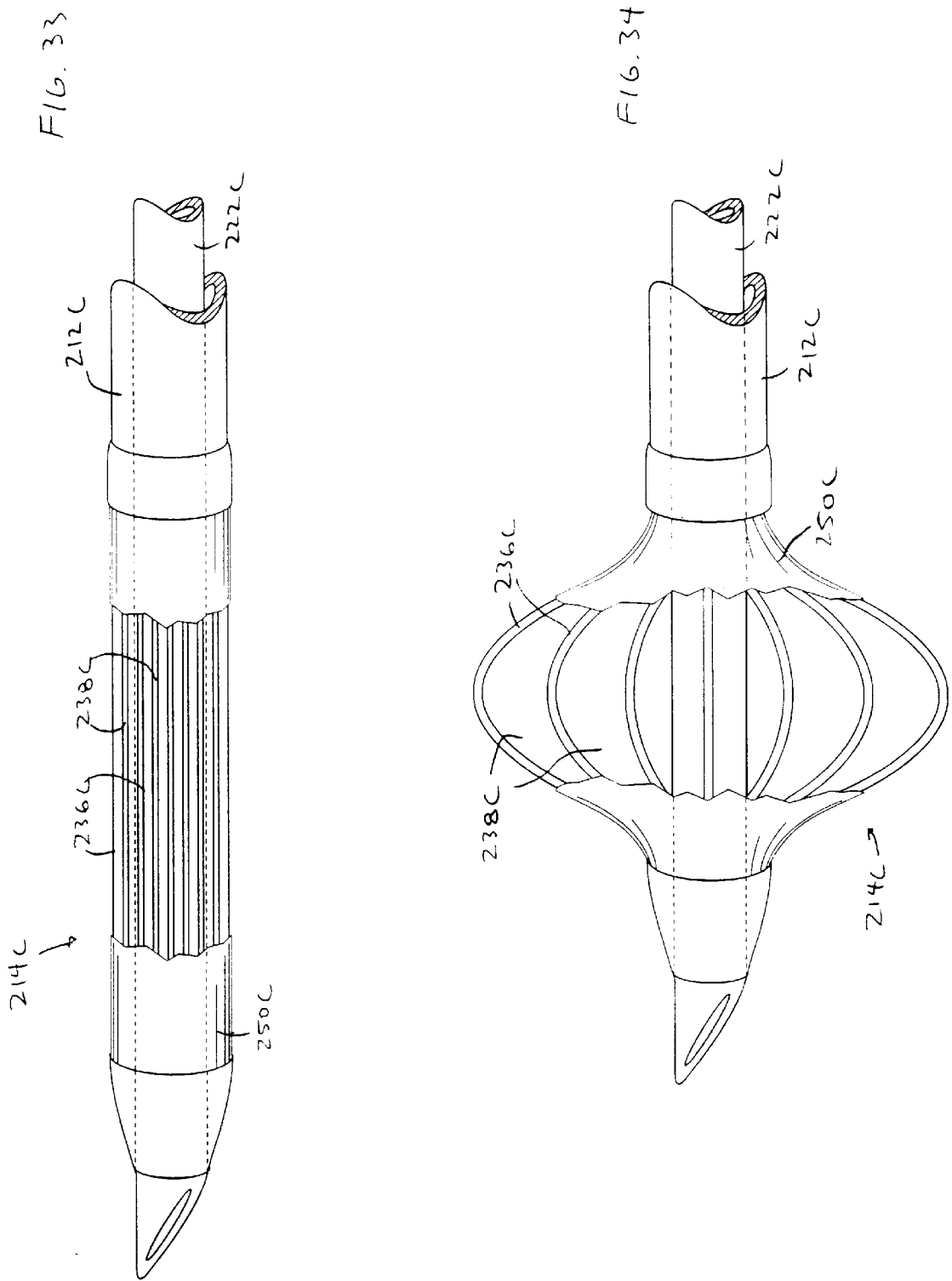

METHODS AND DEVICES FOR OCCLUDING THE ASCENDING AORTA AND MAINTAINING CIRCULATION OF OXYGENATED BLOOD IN THE PATIENT WHEN THE PATIENT'S HEART IS ARRESTED

CROSS-REFERENCE TO RELATED APPLICATIONS

This application is a continuation-in-part of application Ser. No. 09/012,833, filed Jan. 23, 1998, now U.S. Pat. No. 6,159,178, issued Dec. 12, 2000.

BACKGROUND OF THE INVENTION

The present invention is directed to methods and devices for occluding a patient's ascending aorta and maintaining circulation of oxygenated blood in the patient when the patient's heart is arrested. Such devices and methods are useful for performing various procedures on a patient's vascular system and heart such as the procedures described in U.S. Pat. Nos. 5,584,803 and 5,682,906 which describe coronary artery bypass grafting (CABG) and valve procedures, respectively. Another device and method for occluding a patient's ascending aorta is described in Reissue U.S. Pat. No. 35,352.

The methods and devices described in the above-mentioned patents use an internal occlusion device to occlude the ascending aorta rather than a conventional external cross-clamp. Use of an internal occlusion device may reduce strokes as compared to conventional external cross-clamps since external cross-clamps distort and compress the aorta which may release emboli leading to strokes.

It is an object of the invention to provide alternative methods and devices for occluding a patient's ascending aorta and maintaining circulation of oxygenated blood when the patient's heart is arrested.

SUMMARY OF THE INVENTION

In accordance with the object of the invention, the present invention provides alternative methods and devices for occluding a patient's ascending aorta and maintaining circulation of oxygenated blood in a patient when the patient's heart is arrested.

In a first preferred method and device of the present invention, an aortic occlusion device having a blood delivery lumen and an occluding member is introduced into the patient's aortic arch. The occluding member has an interior in fluid communication with the blood delivery lumen so that delivery of oxygenated blood inflates the occluding member. An advantage of this method is that a separate inflation lumen is not necessary. The aortic occlusion device preferably passes through a cannula having a y-arm with the aortic occlusion catheter passing through an arm of the y-arm. The other arm of the y-arm connector is coupled to the source of oxygenated blood so that bypass support can be maintained even when the aortic occlusion device has been removed.

In another preferred method and device, oxygenated blood is delivered to the patient through the aortic occlusion catheter. The aortic occlusion catheter also passes through a cannula with a y-arm connector so that bypass support can be maintained when the aortic occlusion device is removed. The aortic occlusion device also preferably includes a lumen for delivering cardioplegic fluid and venting the ascending aorta and a pressure lumen for measuring pressure in the ascending aorta. If the lumens are not provided in the aortic occlusion device, delivery of cardioplegic fluid, venting of the ascending aorta and pressure monitoring may be accomplished with the cannula.

In another preferred device, the aortic occlusion device has an occluding member mounted to a side of the catheter. The occluding member has a pathway therethrough which is in communication with a lumen in the aortic occlusion catheter. The pathway directs cardioplegic fluid toward the coronary ostia while the aortic occlusion device directs the oxygenated blood in the direction of normal blood flow in the aorta.

According to another aspect of the invention, a device for occluding a patient's aorta comprises a cannula, and an occluding member provided on the cannula that is movable between a collapsed orientation and an expanded orientation, the occluding member being sized and configured to occlude a patient's aorta when in said expanded orientation. The occluding member comprises a non-inflatable structure which has an exterior that is impervious to fluid to substantially prevent fluid flow through a patient's aorta when the occluding member is positioned in the aorta in the expanded orientation.

The non-inflatable structure preferably includes a plurality of individual support elements which move relative to each other as the occluding member moves between the collapsed and expanded orientations, an actuator being provided for moving the occluding member from one to the other of said collapsed and expanded orientations.

These and other aspects and advantages of the present invention will become apparent from the following description and drawings.

BRIEF DESCRIPTION OF THE DRAWINGS

FIG. 18 shows an aortic occlusion device constructed according to another embodiment of the invention, the device including a balloon inflated to occlude the ascending aorta;

FIG. 19 shows the aortic occlusion device of FIG. 18 with the balloon deflated;

FIG. 20 is an elevation view of an aortic occlusion device constructed according to another aspect of the invention, the device being shown positioned in a patient's ascending aorta in a collapsed orientation;

FIG. 21 is an elevation view of the aortic occlusion device of FIG. 20, the device being shown in an expanded orientation to occlude the aorta;

FIG. 22 is an enlarged, partial cut-away view of the aortic occlusion device as shown in FIG. 20;

FIG. 23 is an enlarged, partial cut-away view of the aortic occlusion device as shown in FIG. 21;

FIGS. 26 and 27 are elevation views of an actuator forming part of the aortic occlusion device shown in FIGS. 20 and 21, the actuator being shown in two different positions;

FIG. 28 is a sectional view taken along the line IV–IV in FIG. 26;

FIG. 29 is an elevation, partial cut-away view of an aortic occlusion device constructed according to another embodiment of the invention, the device being shown in a collapsed orientation;

FIG. 30 is a schematic elevation, parital cut-away view showing the device of FIG. 29 in an expanded orientation;

FIG. 31 is an elevation, partial cut-away view of an aortic occlusion device constructed according to another embodiment of the invention, the device being shown in a collapsed orientation;

FIG. 32 is a schematic elevation, partial cut-away view showing the device of FIG. 31 in an expanded orientation;

FIG. 33 is an elevation, partial cut-away view of an aortic occlusion device constructed according to another embodiment of the invention, the device being shown in a collapsed orientation;

FIG. 34 is a schematic elevation, partial cut-away view showing the device of FIG. 33 in an expanded orientation;

DETAILED DESCRIPTION OF PREFERRED EMBODIMENTS

Figure 1:
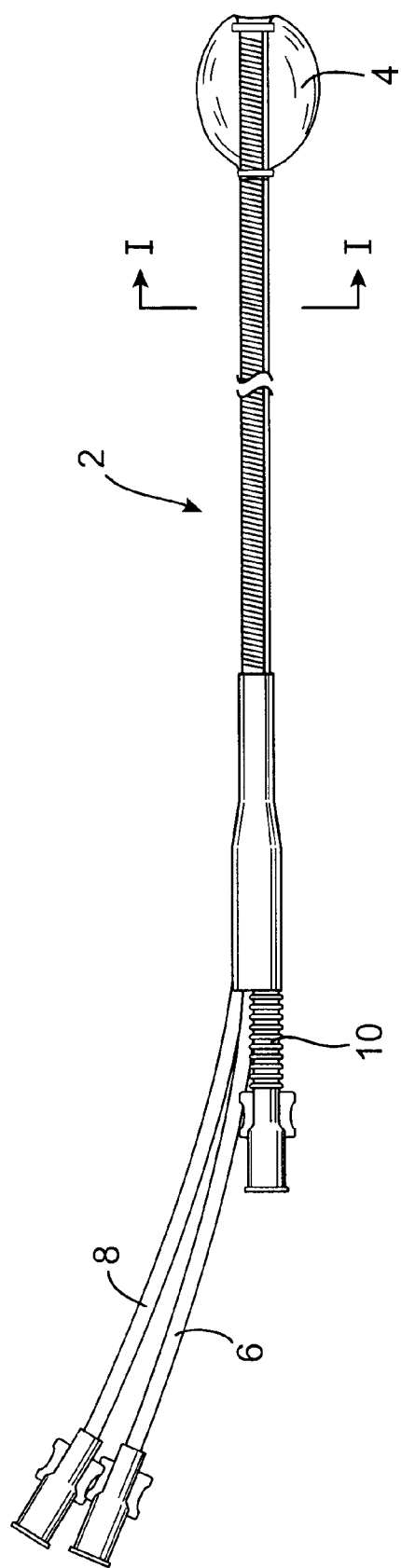
FIG. 1 is an elevation view of an aortic occlusion device constructed according to the invention.
Figure 5:
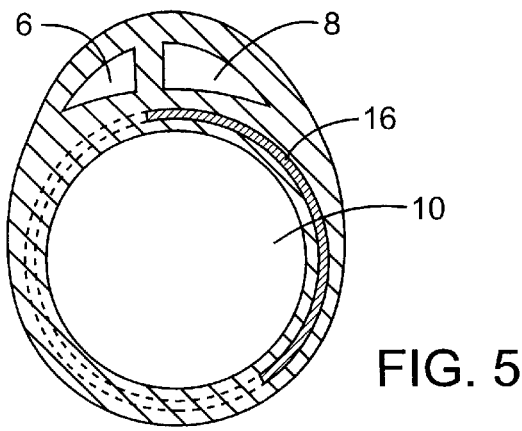
FIG. 5 is a cross-sectional view taken along the line I—I in FIG. 1.

Referring to FIGS. 1 and 5, an aortic occlusion device 2 is shown. The aortic occlusion device 2 has an occluding member 4 configured to occlude a patient's ascending aorta. The occluding member 4 may be a balloon or any of the mechanically actuated members described below. The aortic occlusion device 2 has an inflation lumen 6 for inflating the occluding member 4, a pressure lumen 8 for measuring pressure in the ascending aorta, and a lumen 10 for delivering cardioplegic fluid and/or venting the ascending aorta. The aortic occlusion device 2 is preferably manufactured and used in the manner described in U.S. patent application Ser. No. 08/782,113 but may also be manufactured in any other manner such as an extrusion.

The aortic occlusion device 2 is preferably substantially straight in an unbiased position, however, the aortic occlusion device 2 may also have a shaped end. For example, the aortic occlusion catheter 2 can have an L-shaped end which facilitates positioning the occluding member 4 in the ascending aorta depending upon the surgical approach. The aortic occlusion device 2 is preferably flexible so that it can be bent as necessary without kinking.

Figure 2:
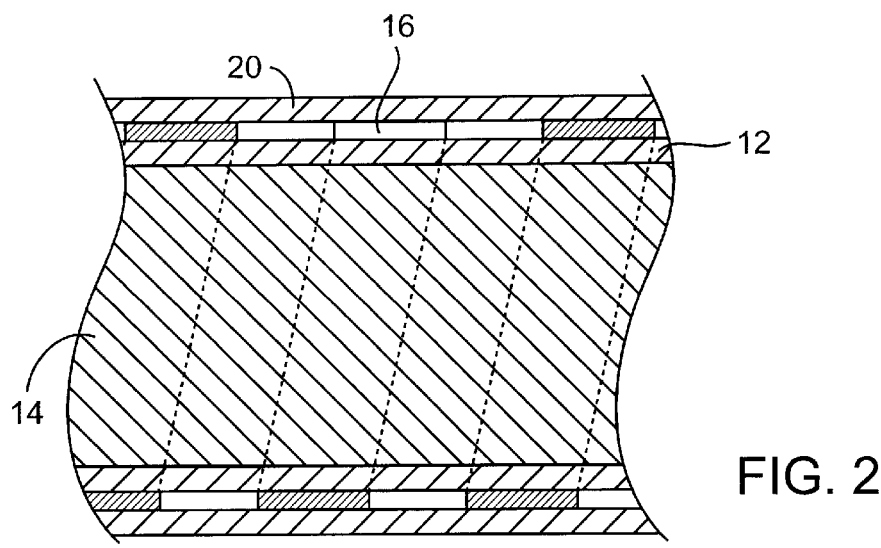
FIG. 2 is a cross-sectional view showing a first step in a process for forming the aortic occlusion device of FIG. 1.
Figure 3:
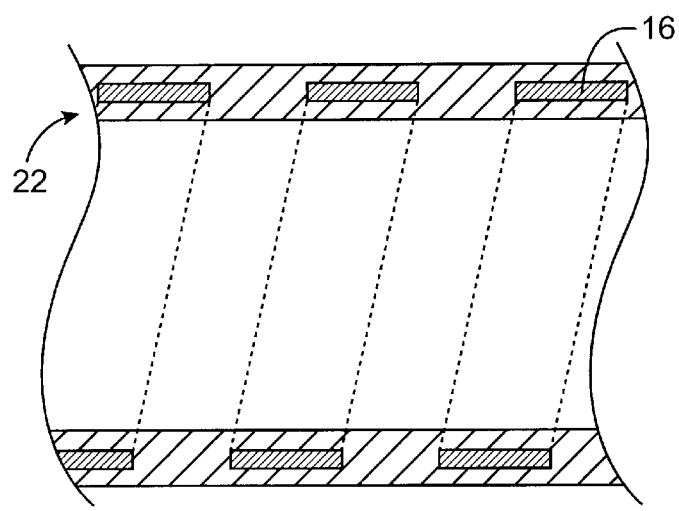
FIG. 3 is a cross-sectional view corresponding to FIG. 2 showing the structure of FIG. 2 after heating.

Referring to FIGS. 2–5, a preferred method of forming the aortic occlusion device 2 is shown. FIG. 2 shows a longitudinal cross-section of a tube 12, preferably a urethane tube, mounted on a teflon-coated mandrel 14 with the elongate element 16 wound helically around the tube 12. The elongate element 16 is preferably a wire ribbon having a thickness of 0.003 inch and a width of 0.012 inch. The elongate element 16 is preferably wrapped around the tube 12 with a spacing of 0.010 inch. Another tube 20 is positioned over the elongate member 16 and a shrink tube (not shown) is positioned over the tube 20. The entire structure is then heated to fuse the tubes together to form a reinforced tube 22 which is shown in longitudinal cross-section in FIG. 3. The resulting reinforced tube 22 preferably has an inner diameter of about 0.100 inch and a wall thickness of about 0.010 inch.

Figure 4:
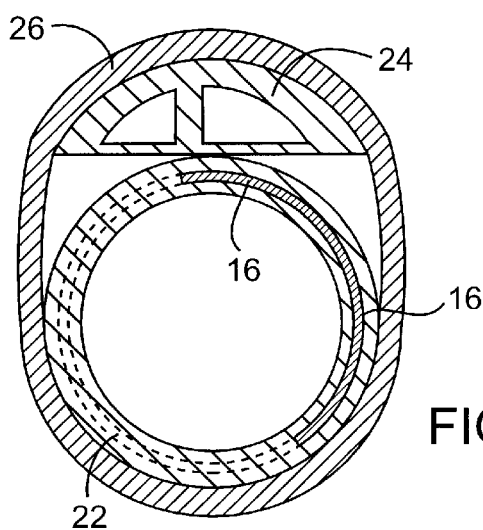
FIG. 4 is a cross-sectional view showing a further step in forming the aortic occlusion device of FIG. 1.

Referring to FIG. 4, a two-lumen member 24 is positioned against the reinforced tube 22 and a shrink tube 26 is positioned around the member 24 and reinforced tube 22. The two-lumen member 24 has the inflation lumen 6, which is used for inflating the occluding member 4, and the pressure lumen 8, which is used for pressure monitoring in the ascending aorta. The two-lumen member 24 is preferably an extrusion having a D-shaped outer surface in cross-section. The member 24 and tube 22 are then heated and the shrink tube 26 is removed to obtain the egg-shaped cross-sectional shape shown in FIG. 5. The cross-sectional shape is preferably about 0.145 inch tall and 0.125 inch wide. The inflation lumen 6 is then pierced to provide an inflation path to the occluding member 4 and the occluding member 4 is then mounted to the shaft.

Figure 6:
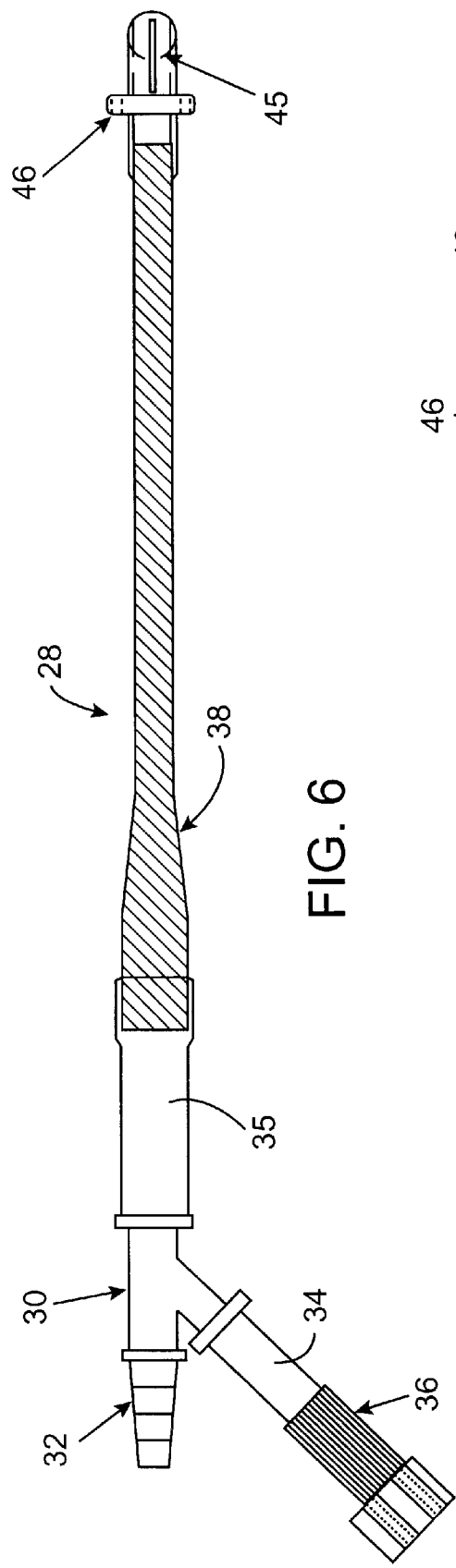
FIG. 6 is an elevation view of a cannula which may be used with the aortic occlusion device of FIG. 1.
Figure 7:
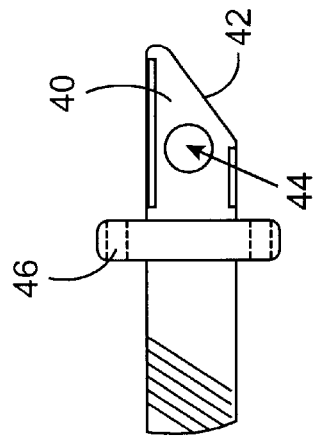
FIG. 7 is an enlarged view of the distal end of the cannula shown in FIG. 6.

Referring to FIGS. 6 and 7, a cannula 28 is shown which is used to return oxygenated blood to the patient. The aortic occlusion device 2 is introduced into the patient through the cannula 28 as will be described below. The cannula 28 has a y-arm connector 30 with first and second arms 32, 34 with each coupled to a lumen 35. The second arm 34 has a hemostasis valve 36 which may be any hemostasis valve and is preferably a Thouy-Borst valve. The cannula 28 has a reinforced body 38 which is preferably formed in the manner described in U.S. patent application Ser. No. 08/749,683, which is hereby incorporated by reference, however, any other method may be used including extrusion. The distal end 40 of the cannula 28 is beveled and has an open end 42 and two side ports 44 for infusing oxygenated blood into the patient. A radiopaque markers 45 are provided at the distal end for visualization as discussed below.

Figure 9:
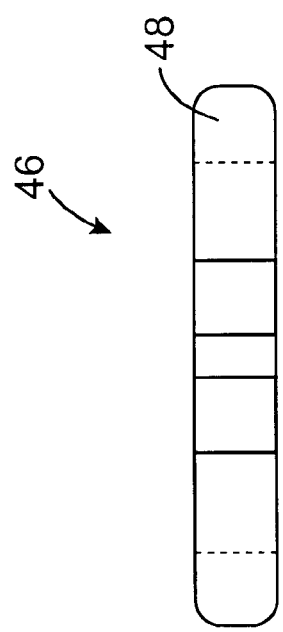
FIG. 9 is a side view of the ring shown in FIG. 8.
Figure 8:
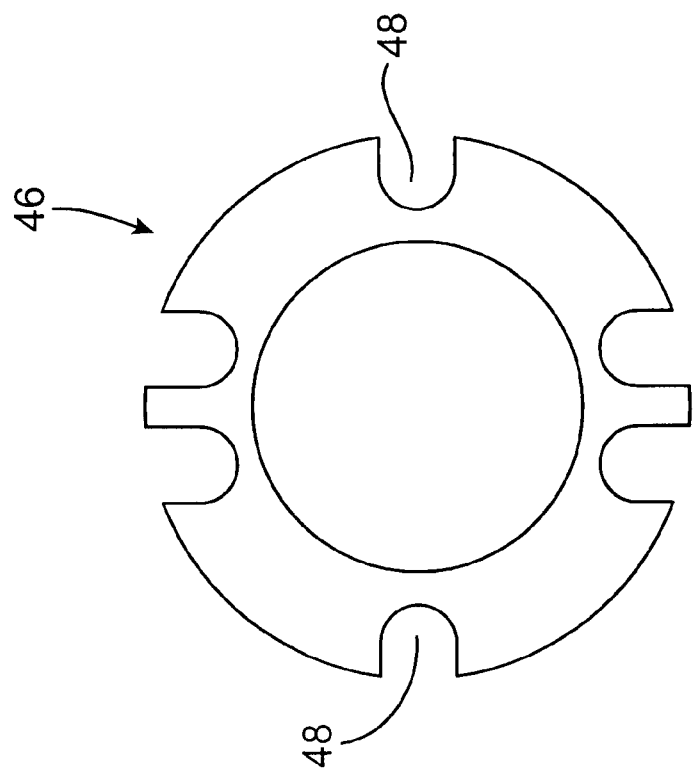
FIG. 8 is a plan view of a ring which may be used with the cannula shown in FIG. 6.

Referring to FIGS. 6–9, a ring 46 is attached to the distal end 40 of the cannula 28. The ring 46 limits insertion of the cannula 28 into the vessel, stabilizes the cannula 28, and receives purse-string sutures which provide hemostasis around the cannula 28 when the cannula 28 is positioned in a vessel. Referring to FIGS. 8 and 9, the ring 46 has slots 48 which may receive purse-string sutures as will be described below.

Figure 10:
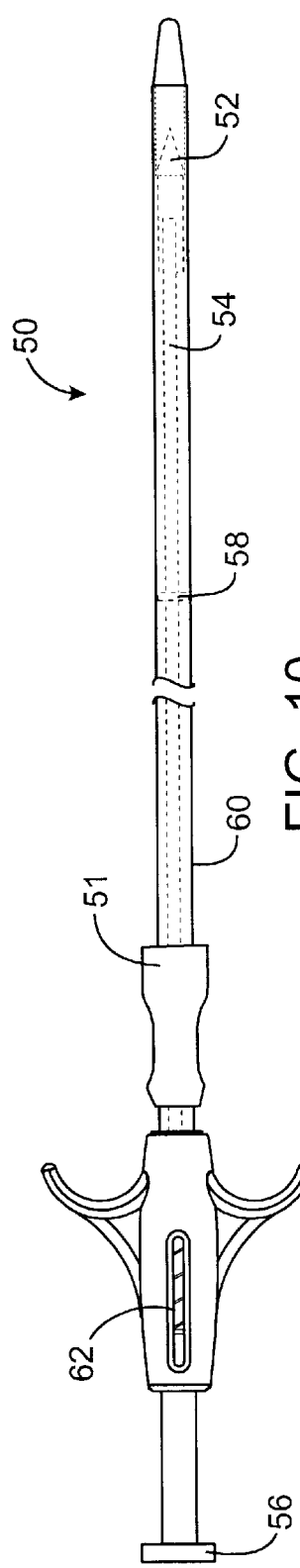
FIG. 10 is an elevation view an introducer which may be used with the cannula shown in FIG. 6, the introducer including an incising element illustrated in a retracted position.
Figure 11:
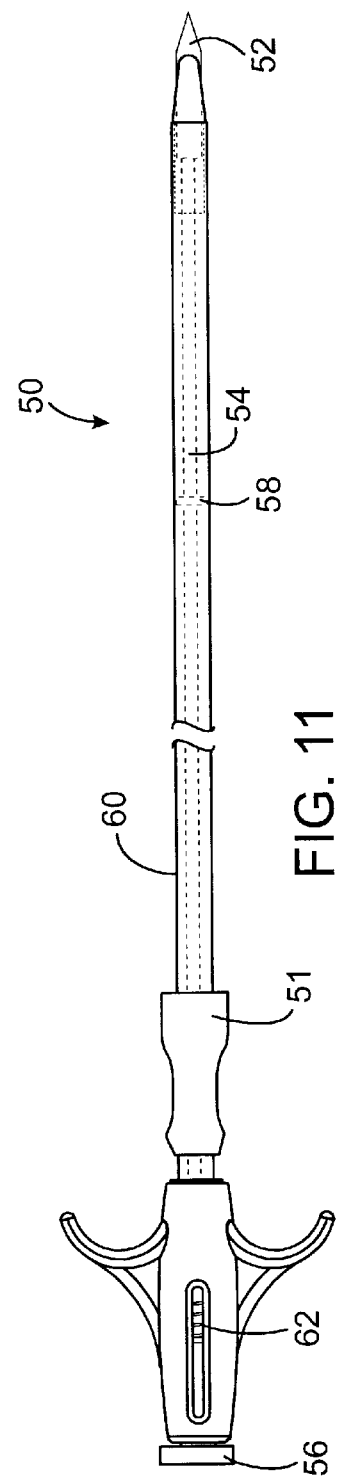
FIG. 11 is an elevation view of the introducer shown in FIG. 10 with the incising element illustrated in an exposed position.

Referring to FIGS. 10 and 11, an introducer 50 is positioned in the cannula 28 to introduce the cannula 28 into a vessel. The introducer 50 has a connector hub 51 which is received by the hemostasis valve 36 on the second arm 32 of the cannula 28 to seal the space between the introducer 50 and cannula 28. The introducer 50 has an incising element 52 for incising the vessel into which the cannula 28 is introduced. The incising element 52 is attached to a shaft 54 which is coupled to a trigger 56 for moving the incising element 52 from the retracted position of FIG. 10 to the exposed position of FIG. 11. An o-ring seals 58 the space between an outer housing 60 and the shaft 54. The incising element 52 is biased toward the retracted position by a spring 62 so that the incising element 52 is only exposed when the trigger 56 is actuated. When introducing the cannula 28 into the vessel, the trigger 56 is actuated to move the incising element 52 to the exposed position, the vessel is incised with the incising element 52 and the cannula 28 is inserted through the incision. As will be described below, one or more purse-string sutures are then used to form a hemostatic seal around the cannula 28. The incising element 52 may be omitted if a separate incising device is used.

Figure 12:
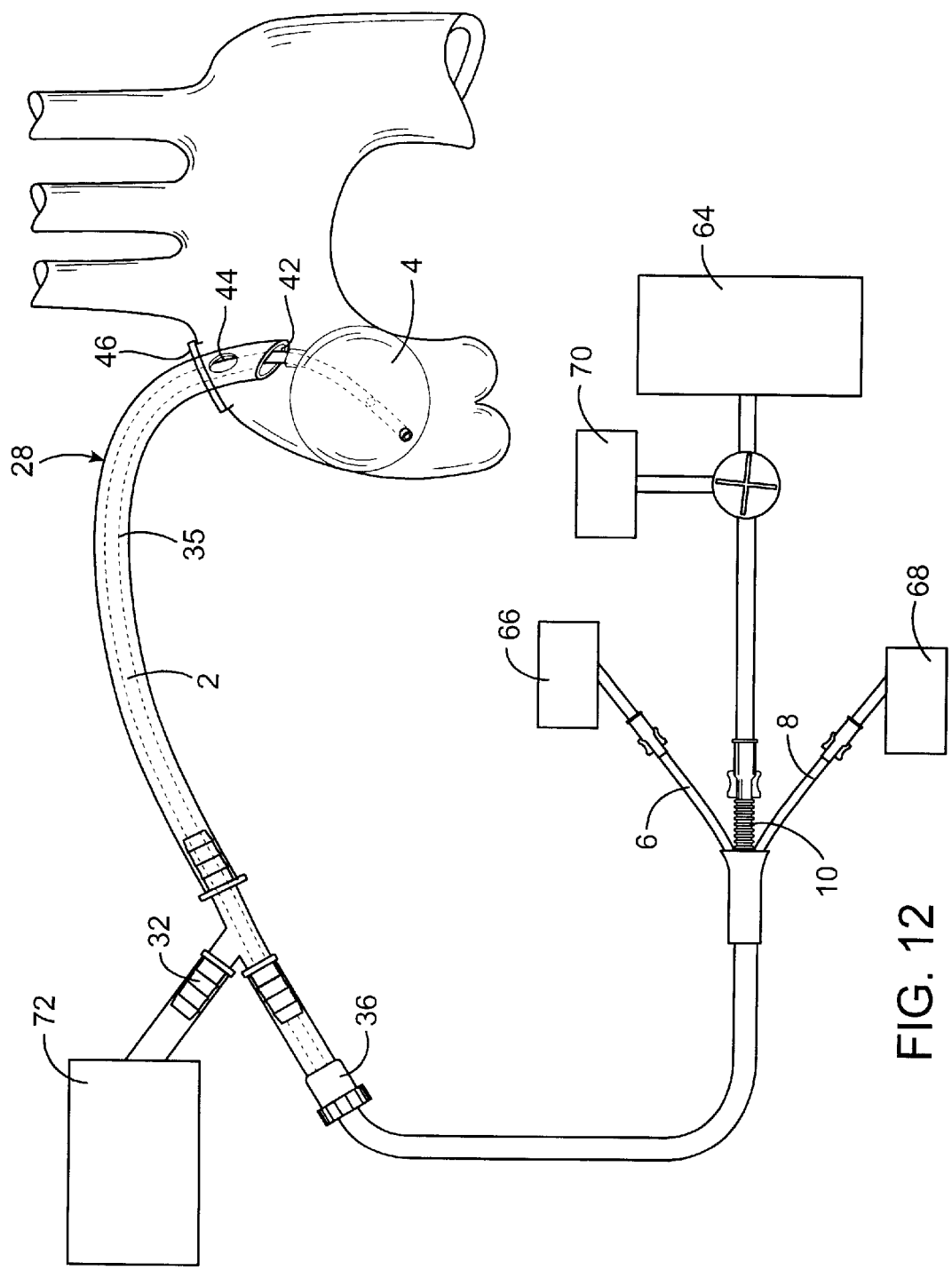
FIG. 12 shows the aortic occlusion device of FIG. 1 and the cannula of FIG. 6 positioned through a penetration in a patient's ascending aorta.

Referring to FIG. 12, the cannula 28 is positioned in a patient's ascending aorta with the aortic occlusion device 2 passing through the hemostasis valve 36. Placement of the cannula 28 and aortic occlusion device 2 into the position of FIG. 12 is described below. Referring to FIGS. 5 and 12, the lumen 10 is coupled to a source of cardioplegic fluid 64, the inflation lumen 6 is coupled to a source of inflation fluid 66, and the pressure lumen 8 is coupled to the pressure monitor 68 for measuring pressure in the ascending aorta. The lumen 10 is also coupled to a vacuum source 70 for venting the ascending aorta.

The first arm 32 of the cannula 28 is coupled to a source of oxygenated blood 72 so that blood is delivered through the lumen 35 of the cannula 28 with the blood passing through the annular area between the cannula 28 and the aortic occlusion device 2. The oxygenated blood passing through the open end 42 of the cannula 28 is directed at the occluding member 4 so that the oxygenated blood is not directed at the wall of the aorta. An advantage of directing the oxygenated blood at the occluding member 4 is that the fluid is dispersed radially outward by the occluding member 4 before coming into contact with the wall of the aorta. By directing the blood at the occluding member 4, rather than at the wall of the aorta, the likelihood of releasing emboli from the wall of the aorta may be reduced. Oxygenated blood is also directed through the side ports 44 so that oxygenated blood is delivered to the patient even if the occluding member 4 blocks the open end 42 of the cannula 28.

Figure 13:
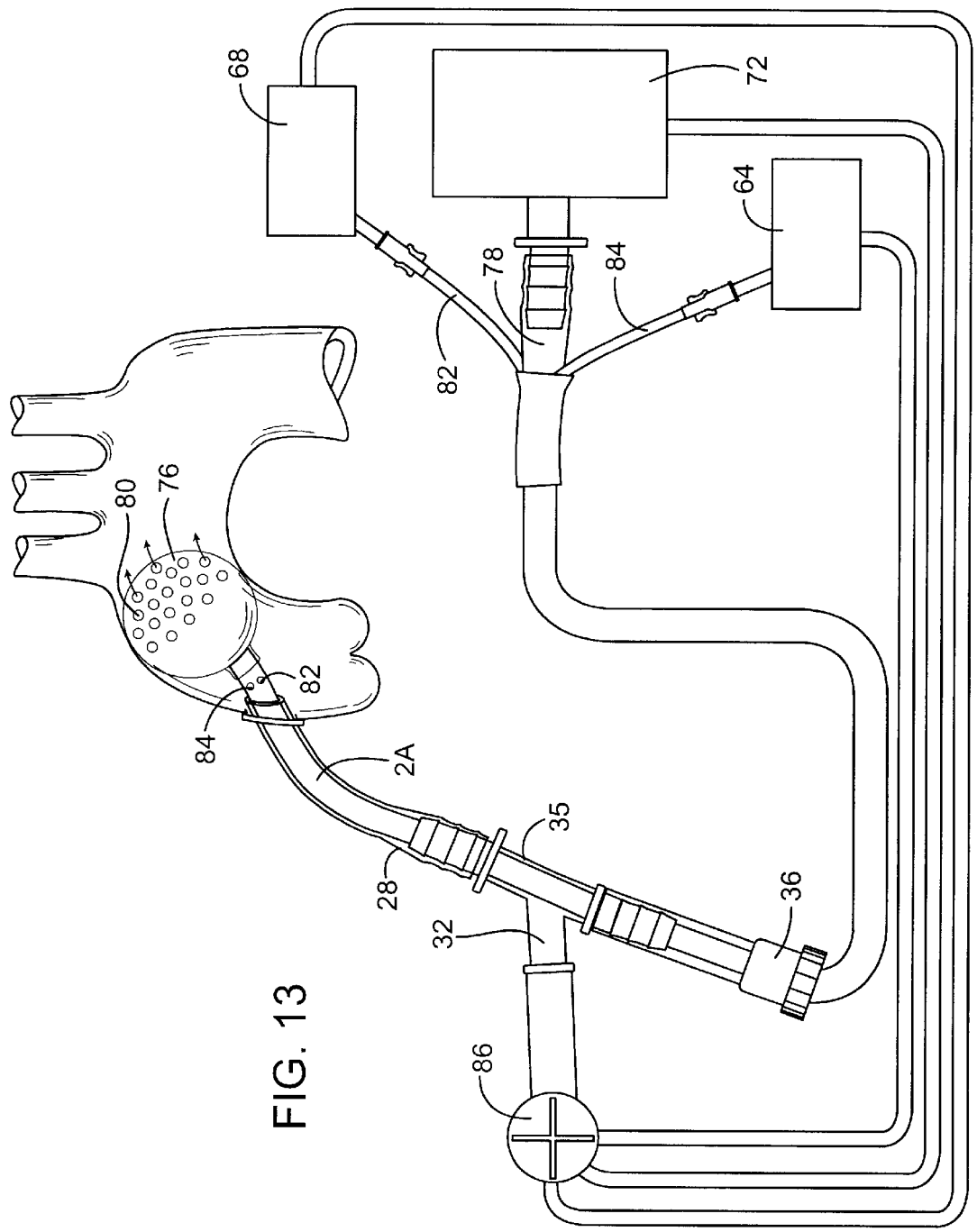
FIG. 13 shows an aortic occlusion device constructed according to another embodiment of the invention, wherein the device is positioned through the cannula and into the patient's ascending aorta.

Referring to FIG. 13, another aortic occlusion device 2A is shown having a balloon 76 which is inflated with the oxygenated blood delivered to the patient. The aortic occlusion device 2A has a blood flow lumen 78 which is fluidly coupled to the interior of the balloon 76 for inflating the balloon 76. Oxygenated blood is then delivered to the patient through an opening 80, preferably a number of openings, in the balloon 76. An advantage of the aortic occlusion device 2A is that a separate inflation lumen is not required since occlusion is accomplished by simply delivering oxygenated blood through the aortic occlusion device 2A. The aortic occlusion device 2A may also include a pressure lumen 82 for measuring pressure in the ascending aorta and a lumen 84 for delivering cardioplegia and venting the ascending aorta. The aortic occlusion device 2A is preferably formed in the manner described above except that the lumen 78 is sized large enough to provide sufficient flow of oxygenated blood at an acceptable pressure. Acceptable blood flow rates and pressures are disclosed in the above-mentioned patents and patent applications which have been incorporated by reference. Although it is preferred to manufacture the device in the manner described above, the aortic occlusion device 2A may also simply be an extrusion or laminated structure. The balloon 76 is preferably made of silicone having a thickness of between 0.005 and 0.009 inch.

The aortic occlusion catheter 2A passes through the cannula 28 so that oxygenated blood can be delivered to the patient when the aortic occlusion device 2A is removed. The cannula 28 is preferably the cannula 28 described above with the first arm 32 coupled to the source of oxygenated blood 72, pressure monitor 68, and source of cardioplegic fluid via valve 86. Thus, cardioplegic fluid and oxygenated blood can be directed through the lumen 35 in the cannula 28 if the lumen 84 is not provided in the aortic occlusion catheter 2A. The cannula 28 has the hemostasis valve 36 to seal the space between the cannula 28 and aortic occlusion device 2A.

Figure 14:
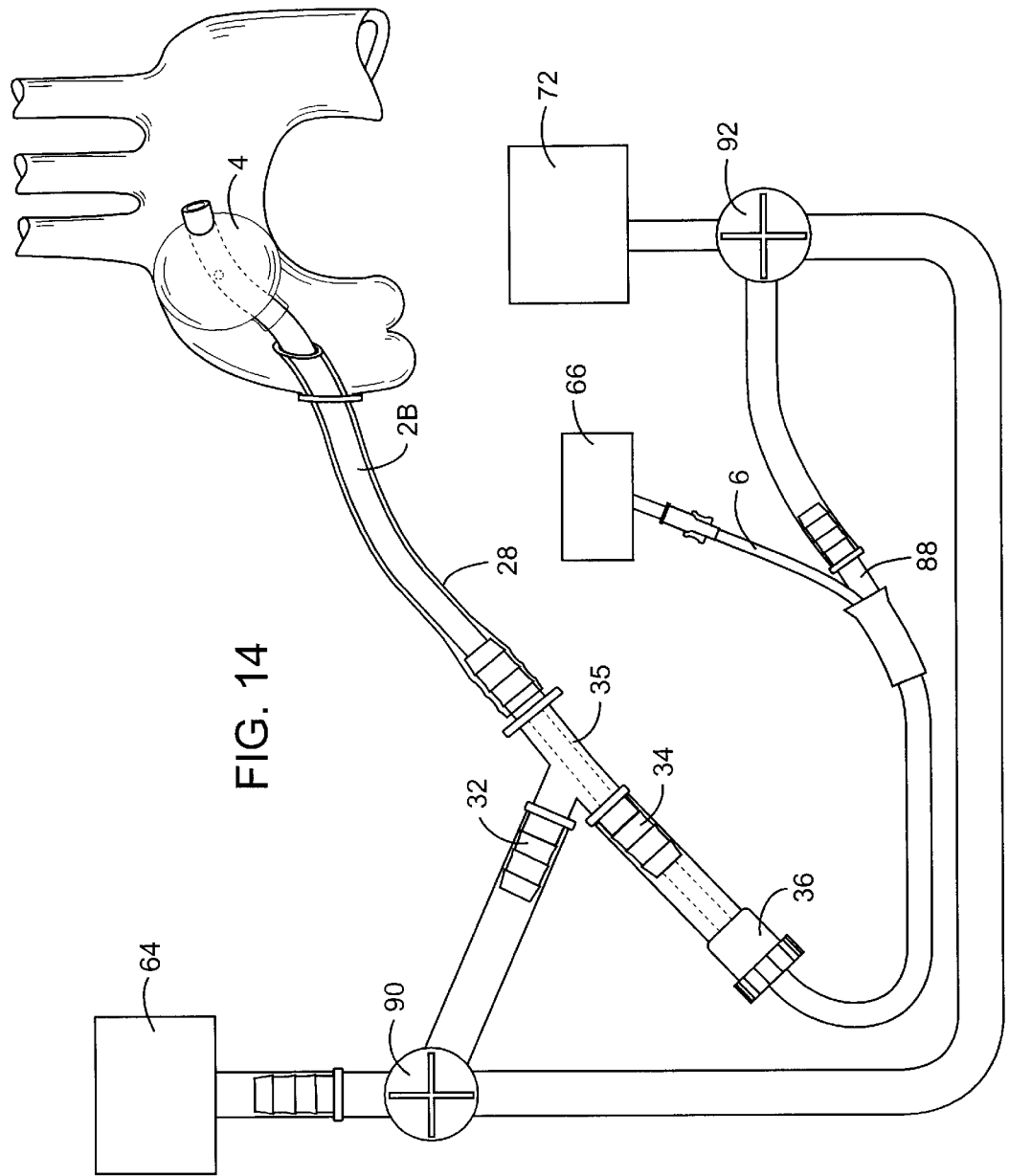
FIG. 14 shows an aortic occlusion device constructed to yet another embodiment of the invention, wherein the device is positioned through the cannula and into the patient's ascending aorta.

Referring to FIG. 14, yet another aortic occlusion device 2B is shown. The aortic occlusion device 2B has the occluding member 4 and the inflation lumen 6 coupled to the source of inflation fluid 66 for inflating the occluding member 4. The aortic occlusion device 2B also has a lumen 88 for delivering oxygenated blood to the patient from the source of oxygenated blood 64. The shaft is preferably reinforced with a wire in the manner described above except that the lumen 88 is sized large enough to provide adequate blood flow to the patient at an acceptable pressure as discussed above. The cannula 28 is preferably the same as the cannula 28 described above and the aortic occlusion device 2B is introduced through the cannula 28 in the manner described below. The first arm 34 of the cannula 28 has the hemostasis valve 36 for receiving the aortic occlusion device 2B. The second arm 32 is coupled to a valve 90 which determines whether cardioplegic fluid or oxygenated blood is delivered through the lumen 35 in the cannula 28. Valve 92 determines whether oxygenated blood is delivered through the lumen 35 in the cannula 28 or the lumen 88 in the aortic occlusion device 2B. An advantage of the aortic occlusion device 2B and cannula 28 is that bypass support can be provided before inflating the occluding member 4 and can also be maintained after the aortic occlusion device 2B is removed from the cannula 28.

Figure 15:
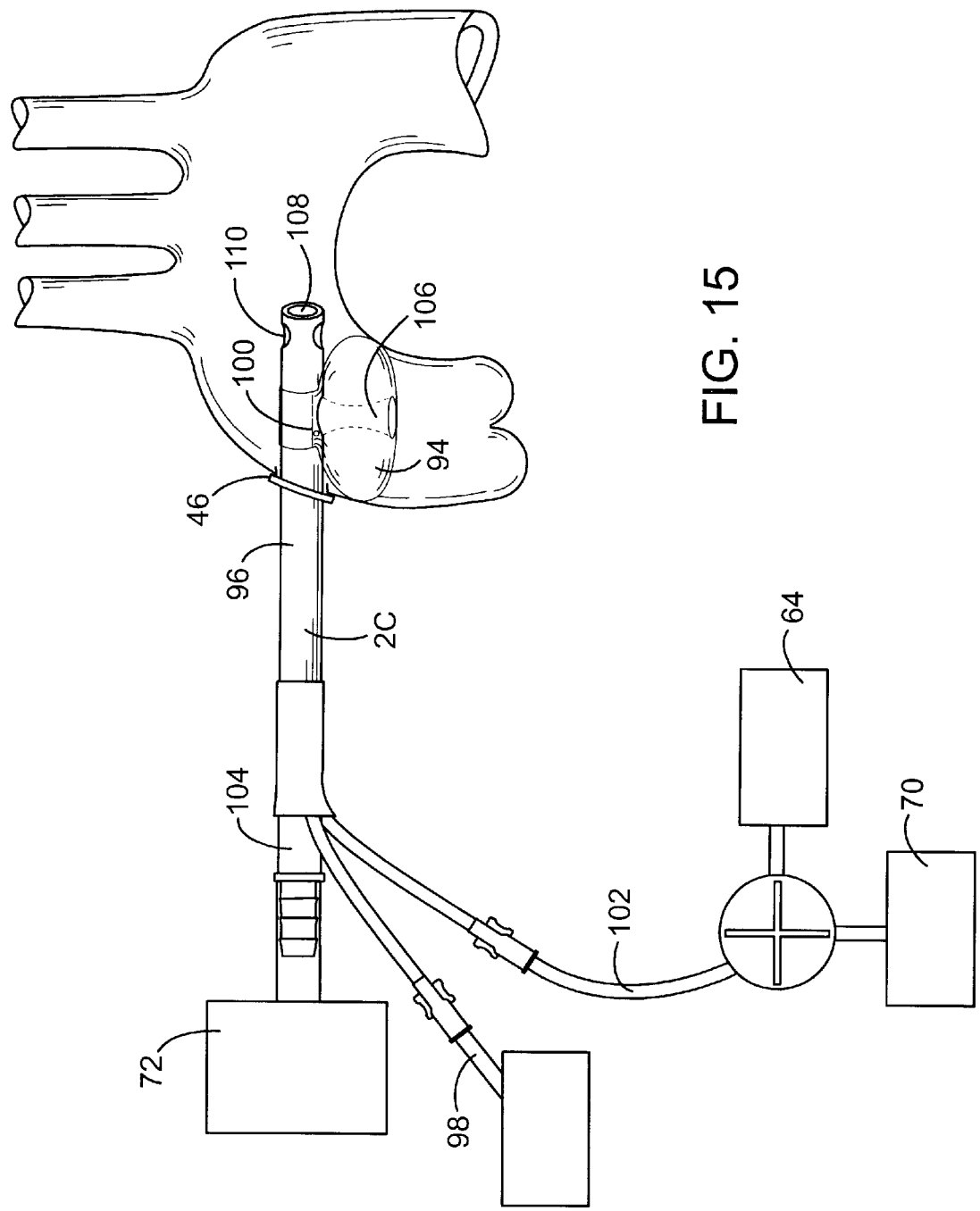
FIG. 15 shows an aortic occlusion device constructed to still another embodiment of the invention, wherein the device is positioned through the cannula and into the patient's ascending aorta.

Referring to FIG. 15, another aortic occlusion device 2C is shown. The aortic occlusion device 2C has a balloon 94 mounted to a side of a shaft 96. The aortic occlusion device 2C has an inflation lumen 98 for inflating the balloon 94 through inflation outlet 100 and a lumen 102 for delivering cardioplegic fluid from the source of cardioplegic fluid 64 and venting the ascending aorta using the vacuum source 70. The aortic occlusion device 2C also has a blood flow lumen 104 for delivering oxygenated blood to the patient from the source of oxygenated blood 72. A fluid path 106 passes through the balloon 94 which is in fluid communication with the lumen 102 so that cardioplegic fluid is delivered through the fluid path 106 in the balloon 94. An advantage of the aortic occlusion device 2C is that the cardioplegic fluid can be delivered toward the aortic valve while oxygenated blood is directed in the direction of normal blood flow in the aortic arch. The distal end of the aortic occlusion device has an open end 108 and side ports 110 through which the oxygenated blood is delivered. The aortic occlusion device 2C also includes the ring 46 which is the same as the ring 46 described above. The aortic occlusion device 2C may be manufactured in any manner such as the manner described above or as a simple extrusion or laminated structure.

Figure 16:
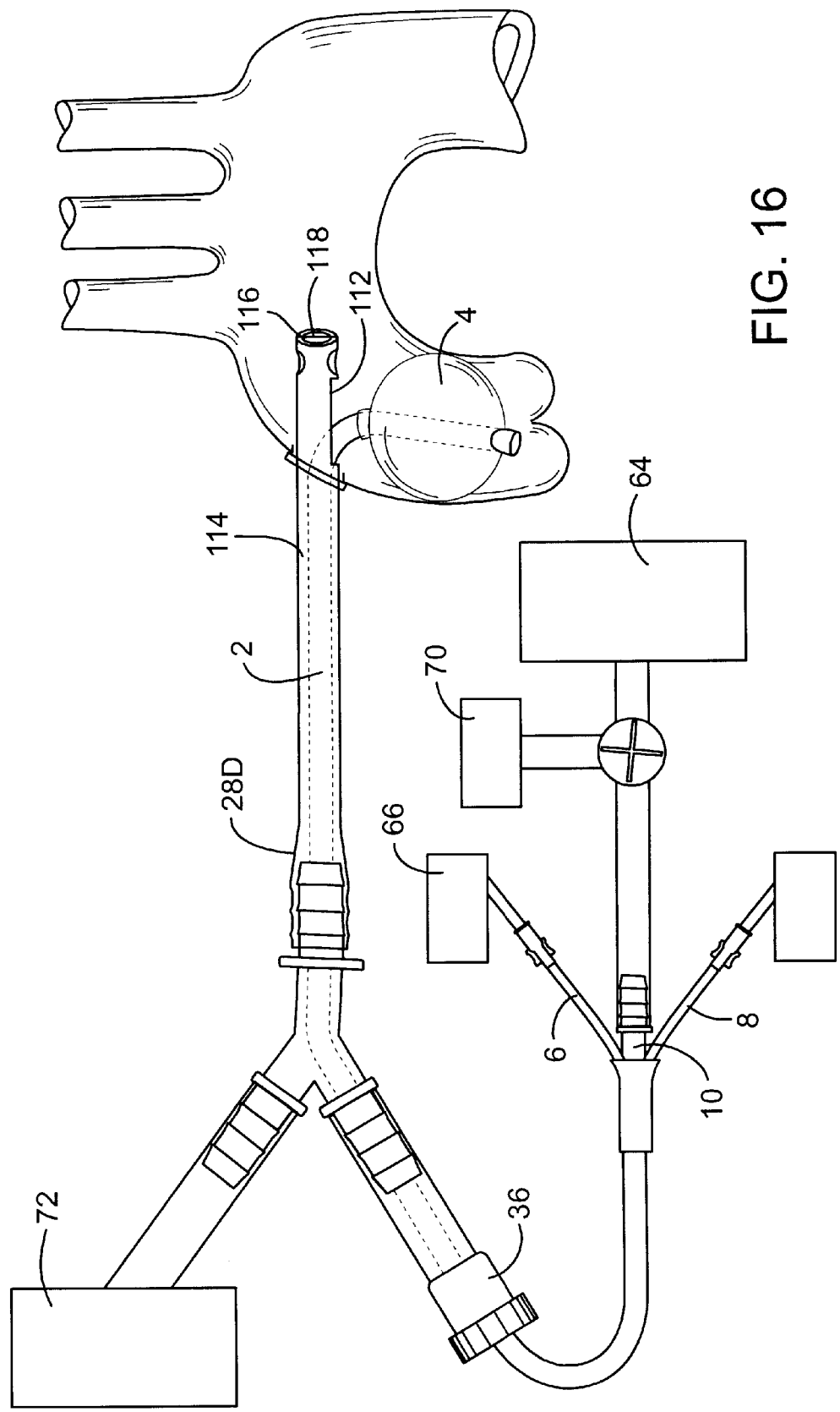
FIG. 16 shows an aortic occlusion device constructed to yet another embodiment of the invention, wherein the device is positioned through the cannula and into the patient's ascending aorta.

Referring to FIG. 16, the aortic occlusion device 2 is shown passing through a side port 112 of a cannula 28D. The side port 112 facilitates positioning the occluding member 4 in the ascending aorta. The aortic occlusion device 2 is preferably the aortic occlusion device 2 described above. The aortic occlusion device 2 passes through a lumen 114 in the cannula 28D. The lumen 114 is coupled to the source of oxygenated blood 72 so that the oxygenated blood is delivered through the annular area between the aortic occlusion device 2 and the wall of the lumen 114. The lumen 114 has an open end 116 with a cross-member 118 which prevents the aortic occlusion catheter 2 from passing through the open end 116. An advantage of the side port 112 is that the aortic occlusion device 2 is directed into the ascending aorta while blood passing through the lumen 114 is directed in the direction of normal blood flow in the aorta.

Referring to FIGS. 18 and 19, another aortic occlusion device 2E is shown. The aortic occlusion device 2E is similar to the aortic occlusion device 2A of FIG. 13 in that balloon 130 is inflated with oxygenated blood delivered from the source of oxygenated blood 72. Oxygenated blood is delivered to the patient through a lumen 132 and an open end 134 of the aortic occlusion device 2E. As will be described below, the interior of the balloon 130 is fluidly coupled to the lumen 132 through an inflation hole 133 for inflating the balloon 130 when blood is delivered through the lumen 132.

The aortic occlusion device 2E includes a body 136 having the y-arm connector 30 described above. A sleeve 138 is positioned in the lumen 132 to control inflation and deflation of the balloon 130. Blood passing through the lumen 132 passes through the sleeve 138 so that the sleeve 138 does not interfere with delivery of oxygenated blood to the patient. The sleeve 138 is attached to a rod 140 which is manipulated to move the sleeve 138 between the positions of FIGS. 18 and 19. The sleeve 138 has a hole 142 which is aligned with the inflation hole 133 as shown in FIG. 18 to fluidly couple the interior of the balloon 130 with the lumen 132. When the sleeve 138 is advanced to the position of FIG. 19, the hole 142 is not aligned with the inflation lumen 133 and the sleeve 138 covers the inflation hole 133 so that the interior of the balloon 130 is not fluidly coupled to the lumen 132.

The sleeve 138 permits the surgeon to control inflation and deflation of the balloon 130. After introduction of the aortic occlusion device 2E, bypass support is generally initiated before inflating the balloon 130. This can be accomplished by maintaining the sleeve 138 in the position of FIG. 19 so that the balloon 130 is not inflated by the blood delivered through the lumen 132. When it is desired to inflate the balloon 130 and occlude the ascending aorta, the sleeve 138 is moved to the position of FIG. 18 so that the balloon 130 is inflated with blood.

The sleeve 138 also permits the surgeon to maintain full occlusion of the ascending aorta even when blood flow is reduced to a level which would not provide sufficient pressure to inflate the balloon to maintain full occlusion of the aorta. In order to maintain occlusion at low flow rates, the sleeve 138 is moved to the position of FIG. 19 before reducing the blood flow rate so that the balloon 130 will remain inflated when the delivery pressure drops. Finally, the sleeve 138 also permits the surgeon to maintain bypass support with a deflated balloon 130 after the surgical procedure is completed. In order to maintain deflation of the balloon while delivering blood, the blood flow rate is reduced to deflate the balloon 130, the sleeve is moved to the position of FIG. 19 to deflate the balloon, and the blood flow rate is then increased. The sleeve 138 prevents the balloon 130 from inflating when the blood flow rate is increased.

The body 136 may be made in any suitable manner and is preferably manufactured similar to the cannula 28 of FIG. 6. A support tube 144 is attached to the body and the balloon 130 is mounted to the support tube. A soft tip 145 is attached to the distal end of the support tube 144 to provide an a traumatic distal end to prevent injury during introduction of the device 2E. The sleeve 138 may be made of any suitable material and is preferably a urethane tube. The rod 140 may also be made of any suitable material and is preferably urethane coated polyamide. Although it is preferred to provide the sleeve 138 between the interior of the balloon 130 and the lumen 132 any other device may be used such as a valve, balloon or plug.

Figure 17:
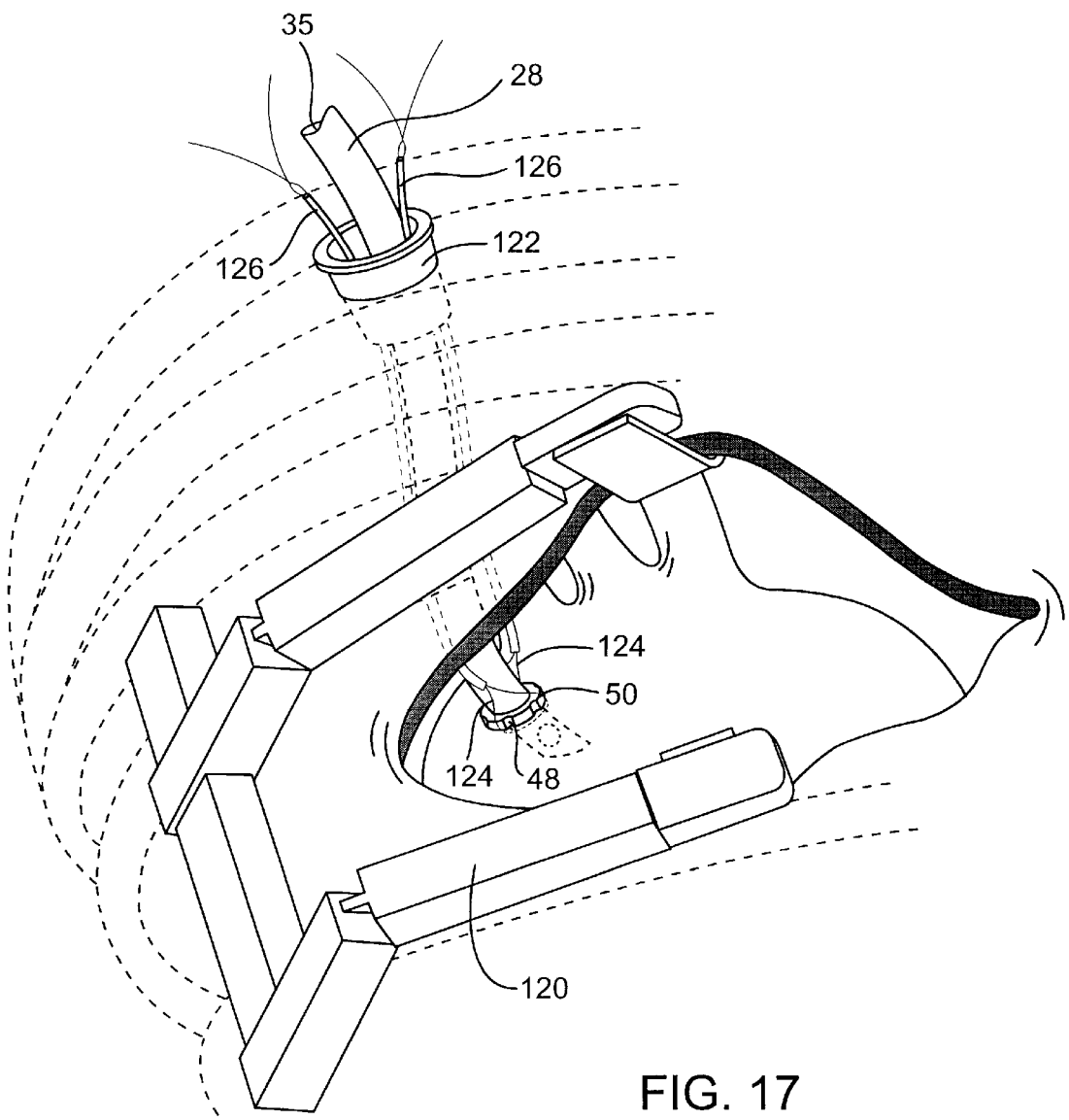
FIG. 17 illustrates a preferred method of introducing the aortic occlusion device into a patient's aorta.

Use of the cannula and aortic occlusion device 2 is now described in connection with FIGS. 12 and 17. The description below is applicable to all cannulae 28, 28D and aortic occlusion devices 2, 2A, 2B, 2C described herein. Although the method described below is for direct insertion of the cannula 28 and aortic occlusion device 2 into the aortic arch, the cannula 28 and aortic occlusion device 2 may also be introduced through a peripheral artery such as the femoral, subclavian or axillary arteries as described in U.S. Pat. No. 5,484,803.

Before introduction of the cannula, a rib retractor 120 or other device is used to form an opening in an intercostal space such as the 4$^{th}$ intercostal space. The opening through the intercostal space is used for access to perform a surgical procedure such as a valve repair or replacement. The opening also provides direct access to the ascending aorta for control of the ascending aorta and to place purse-string sutures in the aorta.

An incision is also created in the 1$^{st}$ or 2$^{nd}$ intercostal space in which an 11.5 mm trocar 122 is positioned. The cannula 28 is then introduced through the trocar 122 and advanced to the surface of the aorta with the introducer 50 (see FIGS. 10 and 11) positioned in the lumen 35 of the cannula 28 to determine the appropriate orientation of the cannula 28. The distal end of the introducer 50 is then moved into contact with the aorta about 1–2 cm below the origin of the innominate artery to identify the appropriate location for purse-string sutures 124. The surgeon then places two purse-string sutures 124 around the site. The ends of the purse-string sutures 124 are passed through tubes 126 which are used to tension the purse-string sutures 124. The purse-string sutures 124 are then passed through the slots 48 in the ring 46.

The cannula 28 is then advanced into contact with the aorta at the site now surrounded by the purse-string sutures 124. The surgeon then incises the aorta with the incising element 52 of the introducer 50 or with a separate incising instrument. The cannula 28 is then immediately advanced through the incision until the ring 46 engages the aorta. The radiopaque marker 45 may be viewed under fluoroscopy and the cannula 28 manipulated until the beveled tip is directed toward the aortic valve. Alternatively, the tip orientation may be determined by TEE. The purse-string 124 sutures are then tensioned to seal around the cannula 28. The aortic occlusion device 2 is then passed through the hemostasis valve 36 and advanced until the occluding member 4 is positioned in the ascending aorta. Delivery of oxygenated blood, occlusion of the ascending aorta and delivery of cardioplegic fluid is then performed in the manner described in U.S. Pat. No. 5,484,803.

Although the method described above positions the aortic occlusion device through an opening separate from the opening through which the surgeon operates, the cannula and aortic occlusion device may also be introduced through the same opening through which the surgeon operates. The choice of opening location, number and size are a matter of surgical choice depending upon patient anatomy, the medical procedure being performed, surgeon preference and the particular embodiment of the invention being used. Furthermore, the devices described herein may have application in other parts of the heart and in other parts of the body. Thus, the description of the specific procedure described above is merely an example and other surgical methods may be used with the devices and methods of the present invention.

Turning now to FIGS. 20–45, aortic occlusion devices constructed according to additional aspects of the invention will be described. In the embodiments discussed below, each device for occluding a patient's aorta utilizes an occluding member which comprises a non-inflatable structure movable between collapsed and expanded orientations. An occluding member in the form of a non-inflatable structure, rather than an inflatable structure such as a balloon, may, for various reasons, be desirable in some applications. For example, a non-inflatable occluding member can be moved between collapsed and expanded orientations without initiating and maintaining inflation via a compressed fluid. In addition, a non-inflatable occluding member may better achieve and retain a desired configuration in its expanded orientation, thereby enhancing occlusion of the aorta, as compared to an inflated occluding member.

Further, there has been some reluctance among surgeons to perform a proximal anastomosis by suturing at a location on the aorta that is near an inflated balloon, due to the risk of the needle piercing and deflating the balloon. The risk of puncturing the balloon is also present when repairing or replacing the aortic valve. To reduce the likelihood of piercing the balloon, some surgeons utilize a side-biting clamp to isolate a portion of the aorta for performing the anastomosis. The use of a side-biting clamp (or other mechanism) to isolate a portion of the aorta may be avoided by utilizing a non-inflatable occluding member because contacting such a member with a needle will not cause the member to collapse immediately and result in loss of occlusion.

The invention provides various specific embodiments of non-inflatable, expandable structures suitable for use on devices for occluding a patient's aorta in order to establish cardiopulmonary bypass. It will be recognized, however, that additional expandable, non-inflatable structures may be used instead.

Generally, in the embodiments described below, the aortic occlusion devices are integrally formed with a cannula in the form of a hollow, tubular shaft that serves to return oxygenated blood to the patient. The occlusion devices of FIGS. 20–41 are not slidably positioned in a separate arterial return cannula, as are the occlusion devices disclosed in connection with several of the embodiments described above. Those skilled in the art will appreciate, however, they may be used with a separate arterial return cannula, as shown, for example, in the embodiment of FIGS. 42 and 43. Thus, any of the aortic occlusion devices described hereinafter may be substituted for the occlusion devices 2, 2A, 2B and 2E described above with respect to previous embodiments. It will, of course, be further appreciated that the occlusion devices of FIGS. 20–43 may be used with other suitable cannulae not specifically disclosed herein.

Moreover, while the aortic occlusion devices are disclosed as being used in a percutaneous procedure in which they are introduced through an intercostal space and directly into a patient's aorta, it will be recognized that they also may be used endovascularly by being introduced into the patient's femoral (or other peripheral) artery, as described above with respect to the previous embodiments.

In the following embodiments, the occluding member comprises a non-inflatable structure that is moved mechanically between the collapsed and expanded orientations. The occluding member has a fluid-impervious exterior that substantially prevents blood flow around the member when it is positioned in an aorta in the expanded orientation. It is desirable that the occluding member completely prevent flow through the aorta; however, as long as flow around the member is substantially prevented the device may still function satisfactorily. The device includes a lumen via which blood is delivered to the patient's circulatory system, the lumen extending from a proximal side of the occluding member to a distal side of the occluding member. The occluding member comprises a plurality of individual support elements which move relative to each other as the member is shifted between the collapsed and expanded orientations. Various forms and configurations of suitable individual support elements are used in the illustrated embodiments; however, it will be recognized that such embodiments are exemplary as other configurations may be used.

With the foregoing in mind, FIGS. 20 and 21 depict a device 210 constructed according to one preferred embodiment of the invention, wherein the device is positioned through an opening formed in the wall of a patient's aorta A. The device 210 comprises a cannula 212 and an occluding member 214 which is movable between a collapsed orientation (FIG. 20) and an expanded orientation (FIG. 21). The cannula 212 is preferably a hollow tubular member having a proximal end 216 provided with a connector, and a distal end 218 provided with a beveled surface for introduction into the patient's body. The body of the cannula may carry a support such as suture ring 219 that rests on the wall of the aorta A. The suture ring 219 may be the same as the suture ring 46 described above. A lumen 220 extends through the cannula 212 and is sized and configured to deliver oxygenated blood to the patient's circulatory system from a cardiopulmonary bypass machine. The lumen 220 may deliver the blood itself or, as in the embodiment of FIGS. 20 and 21, it may receive a tube such as hollow shaft 222 which has a lumen through which the blood is delivered.

Additionally, as shown in FIGS. 20 and 21, the cannula 212 has a lumen 224 coupled to a source of cardioplegic fluid 227 and a pressure lumen 226 coupled to a pressure monitor 229. The lumens 224, 226 extend through the cannula 212 as shown in FIG. 28. Alternatively, the lumens 224, 226 may be secured to and extend along the exterior of the cannula 212. The lumens 224, 226 communicate with openings 228, 231 in the wall of cannula 212 to direct cardioplegic fluid toward the aortic root and arrest the patient's heart. Each lumen 224, 226 is preferably provided with a valve or like mechanism (not shown) for selectively closing the lumens 224, 226.

The proximal end 216 of the cannula 212 is coupled to a source of oxygenated blood 230 which is returned to the patient's circulatory system during cardiopulmonary bypass. The shaft 222 extends through the lumen 220 in the cannula 212 and is connected to the blood source 230 so as to accommodate movement of the shaft 222 upon actuating the device 210, e.g. by a flexible bellows 232. The shaft 222 also passes through and is coupled to an actuator 234 for moving the occluding member 214 between its collapsed (FIG. 20) and expanded (FIG. 21) orientations as will be described in greater detail below.

FIGS. 22 and 23 are enlarged views of the cannula 212 and occluding member 214 wherein the occluding member is shown in its two orientations. The occluding member 214 comprises a plurality of individual support elements which move relative to each other as the member is shifted between the collapsed and expanded orientations. In this embodiment, the individual support elements are in the form of braided elements 236 which overlap each other to form a mesh-like structure. Each of the braided elements 236 comprises a plurality of filaments 238 which are generally parallel to each other. In the illustrated embodiment, each element 236 includes three filaments 238, but, of course, more or fewer filaments may used if desired. Each of the braided elements 236 has a proximal end 240 and a distal end 242 which are secured, respectively, to a proximal section 244 and a distal section 246 of the cannula. These two sections 244, 246 are moved toward or away from each other to move the ends 240, 242 of the braided elements 236 toward or away from each other, thereby expanding or collapsing the occluding member 214.

The proximal section 244 is preferably a sleeve fixed to the body of cannula 212, with the proximal ends 240 of braided elements 236 fixed to the section 244. The respective structures may be secured by any suitable means, e.g., thermal bonding, adhesive, and mechanical fixation. The distal section 246 is also preferably a sleeve and is fixed to the tip 218 of cannula 212, which itself is fixed to the distal end of the actuator shaft 222. The distal ends 242 of the braided elements 236 are secured to the section 246 in the same manner as the proximal ends 240. The beveled tip 218 facilitates introduction of the device through an opening in a patient's body. Upon actuation of the device to expand the occluding member 214, the distal section 246, tip 218, and the distal ends 242 of the braided elements 236 move in unison toward the proximal section 244 and the proximal ends 240 of the braided elements 236. That is, the ends 240, 242 of the braided elements 236 are brought together to expand the occluding member 214.

Figure 25:
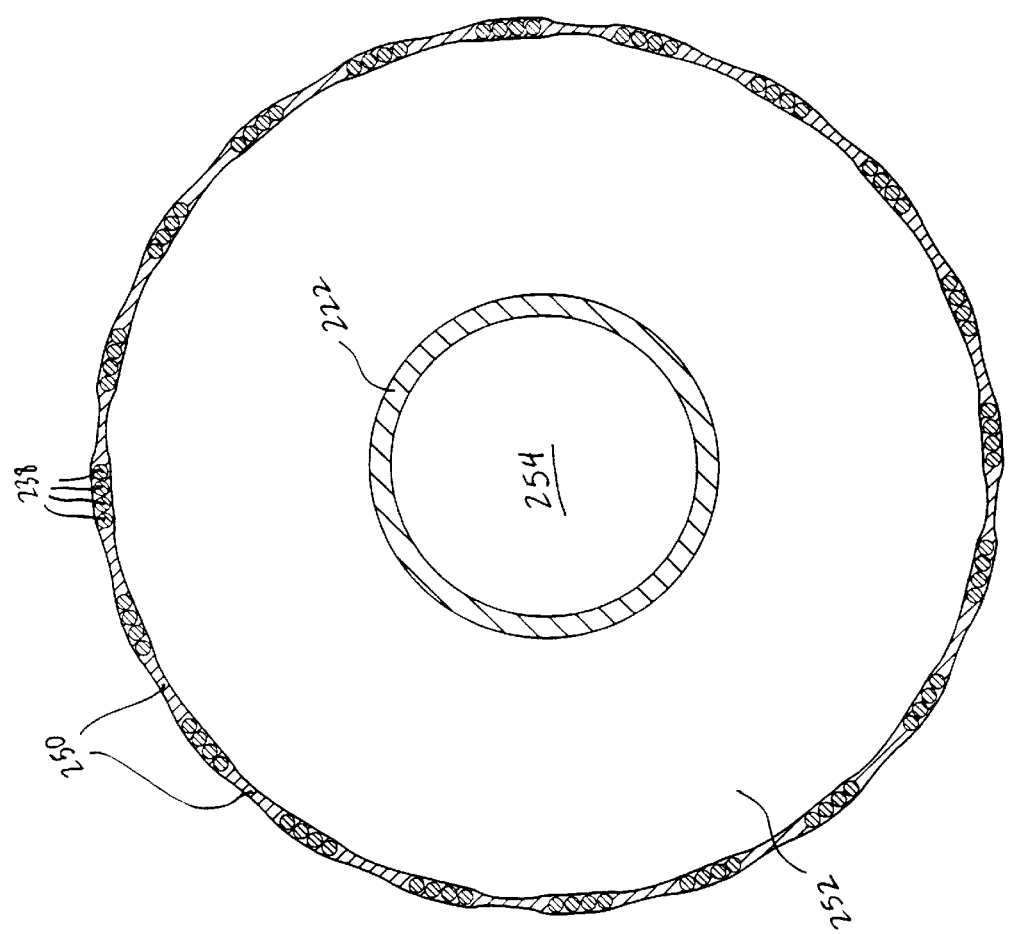
FIG. 25 is a sectional view taken along the line III—III in FIG. 23.
Figure 24:
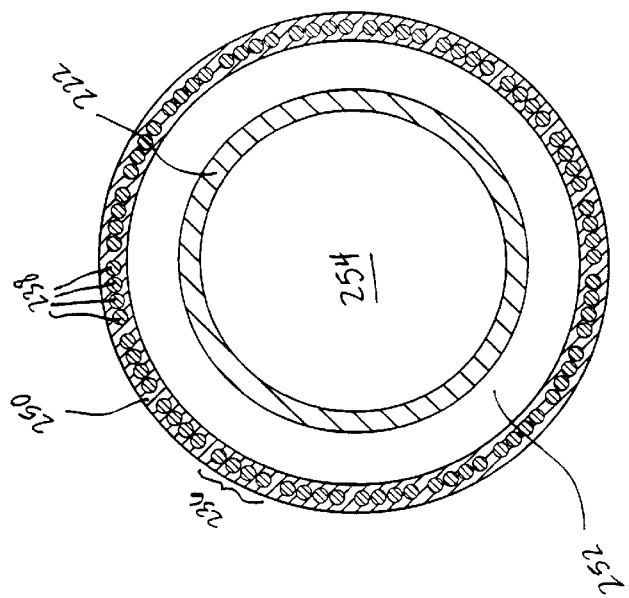
FIG. 24 is a sectional view taken along the line II—II in FIG. 22.

As mentioned above, the occluding member 214 has an exterior that substantially (and preferably completely) prevents the flow of blood around the occluding member when it is positioned in an aorta in its expanded orientation. In the preferred and illustrated embodiment, the occluding member 214 comprises a fluid-impervious material 250 that blocks the open areas between the braided elements 236 to prevent flow therethrough. FIGS. 24 and 25 show the occluding member in its collapsed and expanded orientations, respectively. The fluid-impervious material 250 is sufficiently flexible so that as the braided elements 236 move apart as the occluding member expands, the material 250 stretches to maintain occlusion by the exterior of the occluding member 214.

In the embodiment of FIGS. 20–25, the braided elements 236 contact each other and are generally parallel when the occluding member 214 is in its collapsed orientation. The braided elements 236, however, move apart as the occluding member 214 assumes its expanded orientation to define open areas between adjacent elements. It should be appreciated that the braided elements 236 may be disposed away from each other so that they define open areas when the occluding member 214 is in its collapsed orientation as well. The occluding member has a hollow interior (FIGS. 24 and 25) which defines a lumen 252 through which the shaft 222 is located, the shaft 222 having a lumen 254 which carries blood from the cardiopulmonary bypass machine to the patient's aorta. While the tubular shaft 222 is disposed in the interior of the occluding member 214 and has a lumen for delivering the blood, it is possible to deliver blood through the lumen 252 of the occluding member.

The filaments 238 comprising the braided elements 236 may be formed of any suitable strong, flexible material, including polymers such as polyester (PET), nylon, PEN or PEEK, as well as metals such as spring-tempered stainless steel, nitinol or other superelastic alloys. The fluid-impervious material 250 may be silicone, natural or synthetic rubber, pellethane, KRATON or any other suitable elastomeric material. The occluding element 214 is preferably manufactured by forming a length of the braided structure by any suitable process, such as traditional braiding followed by thermal forming. The braided structure is then dipped in a fluid-impervious material such as silicone. The resulting structure is used to produce an occluding member in which the individual support elements are integrally formed with a fluid-impervious material. As shown in FIGS. 24 and 25, the fluid-impervious material 250 stretches to prevent flow through the open areas defined between braided elements 236. It should be appreciated, however, that other configurations may be used. For example, a flexible sheath or sleeve of silicone, isoprene, polyurethane or other suitable elastomeric materials may be placed over the braided structure and secured thereto, such as by fixing the ends of the sheath to the proximal and distal sleeves 244, 246.

The dimensions of the cannula 212 and the occluding member 214 will vary depending on the particular application, and may be as described above with respect to the previous embodiments. In an exemplary embodiment, at least the distal portion of the cannula 212 has a wire-wrapped configuration (as described above), an OD in the range of from about 18 French to about 25 French, and a length of at least 15 cm. The cannula is preferably configured to permit flow of at least 4.7 liters/min at suitable cardiopulmonary line pressures, preferably less than 300 mm Hg. The occluding member 214 is approximately 2 inches long and has an OD of 0.20 to 0.50 inch, more preferably about 0.25 inch, in its collapsed orientation, and an OD of 1.4 to 2.0 inches, more preferably about 1.75 inch, in the expanded orientation. The preferred dimensions described herein and in incorporated material are applicable to all embodiments described herein.

The occluding member 214 in the illustrated embodiment may be expanded by an amount that produces the desired configuration. For example, in FIG. 21 the occluding member has been expanded to a discoid shape which serves to occlude the aorta while advantageously minimizing the space taken in the aorta for forming an anastomosis or performing a procedure on the aortic valve. In FIG. 23 the occluding member has been expanded to a lesser extent and therefore has rounder shape. The central portion of the expanded occluding member 214 which contacts the wall of the aorta may be various sizes, and preferably is within a longitudinal range of from about 0.5 to about 0.75 inch which corresponds to the maximum OD of 1.4 to 2.0 inch. It will be appreciated that other sizes and shapes may be used if desired.

According to the invention, the occluding member may be formed so that, when unstressed, it assumes either the collapsed or expanded orientation. If expanded when unstressed, the occluding member is forced into its collapsed orientation for introduction into (and removal from) the patient's aorta, and then allowed to return to its expanded orientation when located in the aorta. If collapsed when unstressed, the occluding member is introduced into the patient's aorta and then forced into its expanded orientation to occlude the patient's aorta. The manufacturing process may be carried out to determine which orientation the occluding member assumes when unstressed.

The invention further comprises the actuator 234 for selectively moving the occluding member 214 between the collapsed and expanded orientations. The actuator 234, shown in FIGS. 26 and 27, comprises a body 256 secured to the cannula 212 and a handle 258 slidably positioned in the body. The body 256 has an interior 260 which forms an extension of the lumen 220 of the cannula 212. The handle 258 is secured to the shaft 222. For example, the handle 258 may have a bore 262 in which the shaft 222 is fixed. In the illustrated embodiment, the shaft 222 passes through the actuator handle and extends to the oxygenated blood supply 230. The shaft 222 could also terminate at the actuator handle 258 and communicate with tubing extending from the handle to the blood supply 230.

The actuator handle 258 has a portion 264 which is grasped by a user and moved relative to the actuator body 256 to move the shaft 222 relative to the cannula 212. The actuator body 256 may be provided with finger loops 268 (or other structure) for easy handling of the device during use. A spring 270 is disposed in the actuator body 256 and biases the actuator handle 258 to a desired position.

The handle 258 is moved from the position of FIG. 26 to the position of FIG. 27 to move the shaft 222 rearward. In the embodiment shown in FIGS. 20 and 21, the actuator 234 is used to move the occluding member 214 from its collapsed orientation (FIG. 20) to its expanded orientation (FIG. 21). Thus, in this embodiment the occluding member is collapsed when the actuator is as shown in FIG. 26. The actuator handle 258 is moved away from the actuator body 256 (to the position of FIG. 27) to pull the shaft 222 rearward with respect to the cannula 212. The distal end of the shaft 222 is fixed to the tip 218; thus, moving the end of the shaft 222 moves the distal section 246 and ends 242 of the braided elements 236 (FIG. 23). This brings the ends 240, 242 of the braided elements 236 together to expand the occluding member 214.

The actuator 234 preferably has a mechanism for securing the handle 258 (and shaft 222) with respect to the actuator body 256 (and the cannula 212). For example, the handle 258 may have a pawl 272 that engages ratchet teeth 274 on the interior of the actuator body 256 to fix the position of the shaft 222 (FIGS. 26 and 27). The pawl 272 may be biased toward the actuator body 256 by a spring (not shown) so that the pawl must be depressed to disengage the handle 258 and the body 256, however, any suitable alternative locking mechanism may be used.

In the illustrated embodiment, the occluding member is collapsed when the actuator 234 is at rest, and is expanded by actuating the handle 258 and locking it in position. As noted above, however, the invention may be constructed so that the occluding member 214 is expanded when the actuator 234 is at rest. For example, the actuator 234 would be in the position of FIG. 26 when the occluding member 214 is expanded, and in the position of FIG. 27 when the occluding member is collapsed. If constructed in this manner, the actuator would be actuated to collapse the occluding member for introducing the device into the patient's aorta, and then released to allow the occluding member to return to its expanded orientation. The occluding member thus would not require continuous force to maintain it in its expanded orientation while in the aorta. It will be readily understood that alternative actuating mechanisms can be used to move the occluding member between its collapsed and expanded orientations.

FIGS. 29 and 30 show an alternative embodiment of the invention wherein the occluding member has a different construction than that of occluding member 214 described above. The cannula, indicated by reference numeral 212A, has an occluding member 214A which is shown, respectively, in its collapsed and expanded orientations in FIGS. 29 and 30. The occluding member 214A, like the member 214, comprises a plurality of individual support elements which move relative to each other as the member is shifted between the collapsed and expanded orientations. In this embodiment, the individual support elements are in the form of cross members 236A connected to each other so as to define spaces 238A therebetween.

The cross members 236A form a grid-like structure and move relative to each other as the occluding member 214A moves between the orientations of FIGS. 29 and 30. The device is actuated by a shaft 222A as described above with respect to the previous embodiments. The cross members 236A may be formed of any suitable polymeric or metallic material including superelastic materials such as nitinol. The occluding member 214A has an exterior that substantially (and preferably completely) prevents the flow of blood around the occluding member when it is positioned in an aorta in its expanded orientation. The occluding member 214A is preferably provided with a fluid-impervious material 250A that blocks the open areas between the cross members 236A. The material 250A may be integrally formed with the occluding member 214A, for example, by dipping the member in silicone, or a separate sheath of such material may be secured to the member.

FIGS. 31 and 32 show another alternative embodiment of the invention comprising a cannula 212B and an occluding member 214B shown, respectively, in collapsed and expanded orientations. The occluding member 214B comprises a plurality of individual support elements which move relative to each other and the member is shifted between the collapsed and expanded orientations. The individual support elements are in the form of helical coils 236B connected to each other so as to define spaces 238B therebetween.

The coils 236B move relative to each other as the occluding member 214B moves between the orientations of FIGS. 31 and 32, which is accomplished by moving an actuator shaft 222B as described above with respect to the previous embodiments. The coils 236B are preferably naturally biased toward the expanded orientation although they may be naturally biased toward the collapsed orientation. The coils 236B may be formed of any suitable polymeric or metallic material, such as spring wire, stainless steel or superelastic materials such as nitinol. The occluding member 214B has an exterior that substantially (and preferably completely) prevents the flow of blood around the occluding member when it is positioned in an aorta in its expanded orientation. As in the above embodiments, the occluding member 214B is preferably provided with a fluid-impervious material 250B that blocks the open areas between the coils 236B. The material 250B may be integrally formed with the occluding member 214B, for example, by dipping the member in silicone, or a separate sheath of such material may be secured to the member.

FIGS. 33 and 34 show still another alternative embodiment of the invention which comprises a cannula 212C and an occluding member 214C which are shown, respectively, in collapsed and expanded orientations. The occluding member 214B comprises a plurality of individual support elements in the form of flexible struts 236C disposed adjacent to each other to define spaces 238C therebetween, the proximal and distal ends of the struts being fixed to the shaft 222C and the cannula 212C, respectively.

The struts 236C move relative to each other as the occluding member 214C moves between the orientations of FIGS. 33 and 34, which is accomplished using the actuator described above with respect to the previous embodiments. The struts 236C may be formed of any suitable polymeric or metallic material, such as nitinol or spring tempered steel. As above, the occluding member 214C has an exterior that substantially (and preferably completely) prevents the flow of blood around the occluding member when it is positioned in the aorta in its expanded orientation. The occluding member 214C is preferably provided with a fluid-impervious material 250C that blocks the open areas between the struts 236C. The material 250C may be integrally formed with the occluding member 214C, for example, by dipping the member in silicone, or, alternatively, a separate sheath of such material may be secured to the member.

Figure 35:
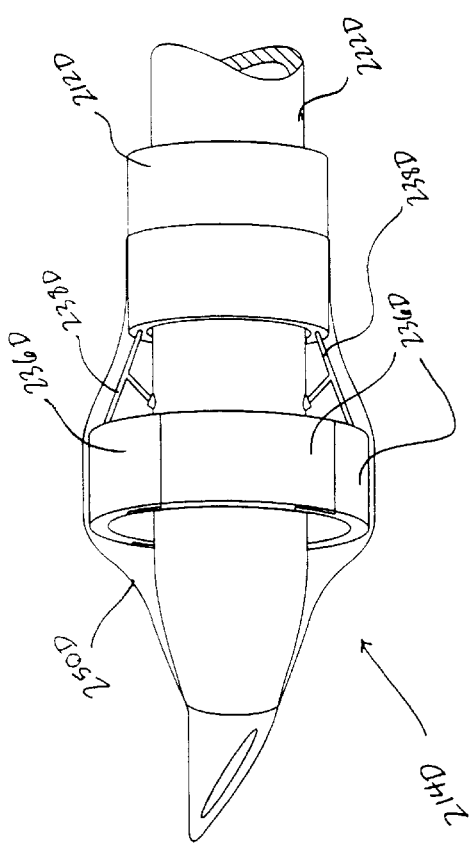
FIG. 35 is an elevation view of an aortic occlusion device constructed according to another embodiment of the invention, the device being shown in a collapsed orientation.
Figure 36:
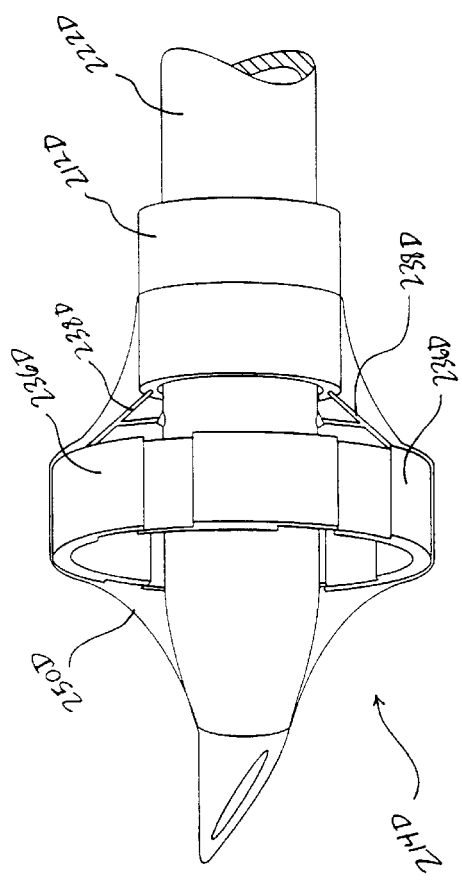
FIG. 36 is an elevation view of the device of FIG. 35 in an expanded orientation.

Referring now to FIGS. 35 and 36, yet another alternative embodiment of the invention is shown. This embodiment includes a cannula 212D and an occluding member 214D which are shown, respectively, in collapsed and expanded orientations. The occluding member 214D comprises a plurality of individual support elements in the form of overlapping segments 236D which are moved with respect to each other by a plurality of arms 238D. The arms 238D comprise three portions which are pivotally connected to the proximal cannula sleeve 244D, the shaft 222D, and the overlapping segments 236D.

As the shaft 222D is moved in a proximal direction (to the left as viewed in FIGS. 36 and 37), the arms 236D pivot on the respective members to which they are attached, which forces the overlapping segments 236D apart to expand the occluding member 214D. The occluding member 214D is moved between the orientations of FIGS. 36 and 37 using the actuator described above with respect to the previous embodiments. The overlapping segments 236D and the arms 238D may be formed of any suitable polymeric or metallic material, such as nitinol or spring tempered steel The occluding member 214D has an exterior that substantially (and preferably completely) prevents the flow of blood around the occluding member when it is positioned in the aorta in its expanded orientation. The occluding member 214D is preferably provided with a fluid-impervious material 250D that blocks the open areas proximal and distal to the segments 236D. The material 250D may be integrally formed with the occluding member 214D, for example, by dipping the member in silicone, or, alternatively, a separate sheath of such material may be secured to the member.

Figure 37:
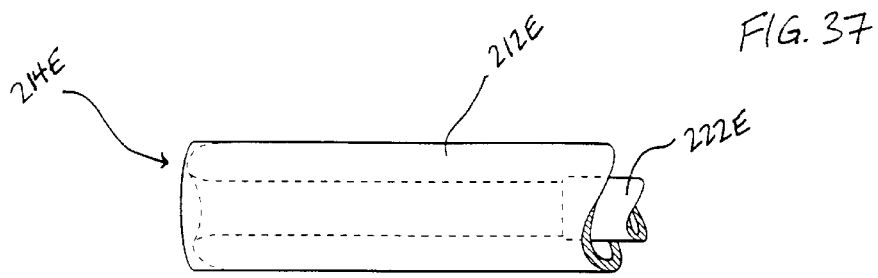
FIG. 37 is a schematic elevation view of an aortic occlusion device constructed according to another embodiment of the invention, the device being shown in a collapsed orientation.
Figure 38:
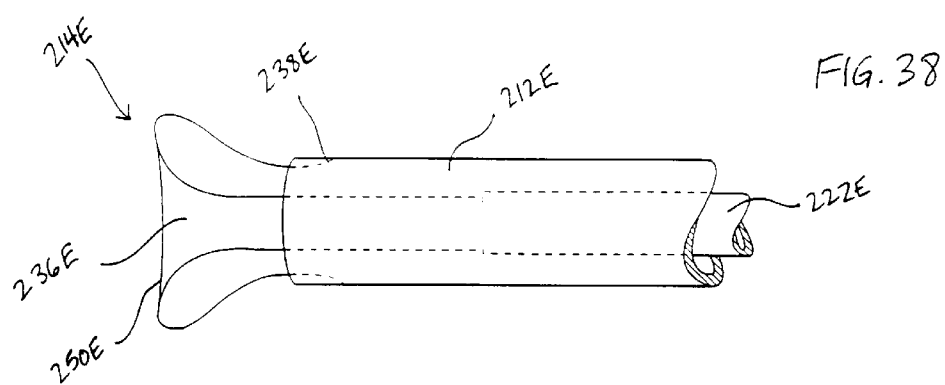
FIG. 38 is a schematic elevation view showing the device of FIG. 37 in a partially expanded orientation.
Figure 39:
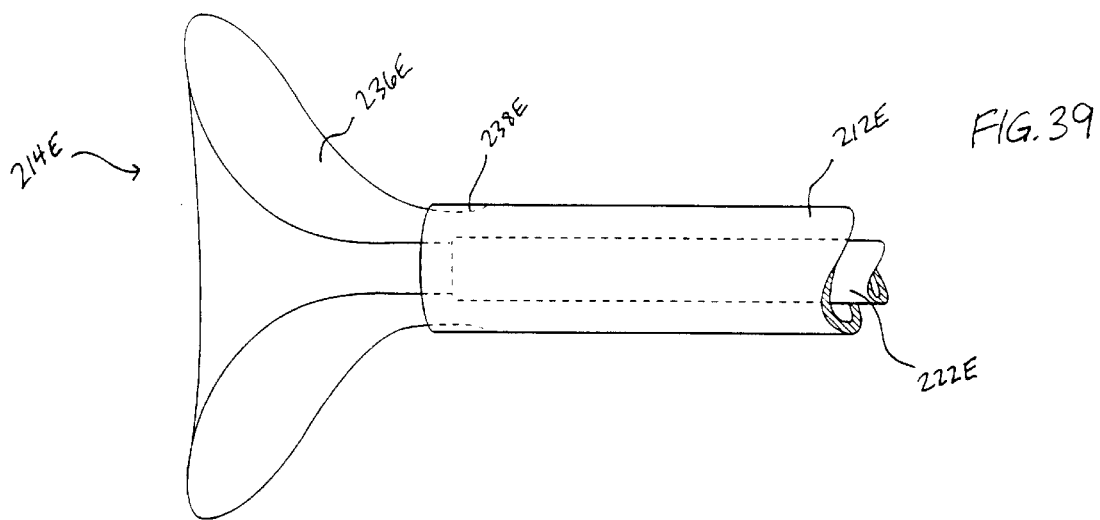
FIG. 39 is a schematic elevation view showing the device of FIG. 37 in a fully expanded orientation.

Still another embodiment of the invention is shown in FIGS. 37–41 and comprises a cannula 212E and an occluding member 214E which is shown collapsed in FIG. 37 and expanded in FIG. 39. The occluding member 214E comprises a plurality of individual support elements in the form of braided elements 236E which overlap each other to form a mesh-like structure. Each of the braided elements 236E comprises a plurality of filaments 238E as described above with respect to the embodiment of FIGS. 22 and 23. In this embodiment, however, the occluding member 214E is preferably completely enclosed in the cannula 212E when in the collapsed position, as shown in FIG. 37. The occluding member 214E has one end 240E fixed to the end of the shaft 222E, and another end 242E fixed to the cannula 212E.

The occluding member 214E is moved by moving the shaft 222E with respect to the cannula 212E. In the illustrated embodiment, the shaft 222E is moved distally to force the occluding member 214E out of the cannula 212E. FIGS. 37–39 show sequentially the occluding member being moved to its expanded orientation. The occluding member is preferably manufactured so that it is expanded (FIG. 39) when unstressed. As such, the shaft 222E is moved proximally relative to the cannula 212E to collapse the occluding member 214E for introduction into (and removal from) the aorta. Once positioned in the aorta, the shaft 222E is moved distally to return the occluding member 214E to its expanded orientation.

Figure 40:
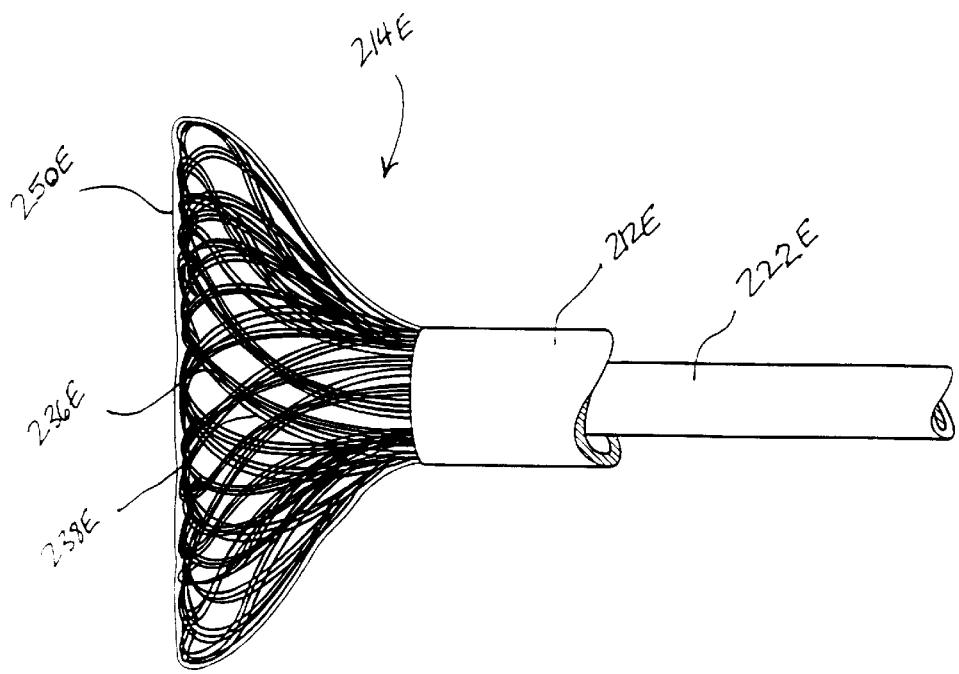
FIG. 40 is an elevation view showing the device shown in FIG. 37 in its fully expanded orientation.
Figure 41:
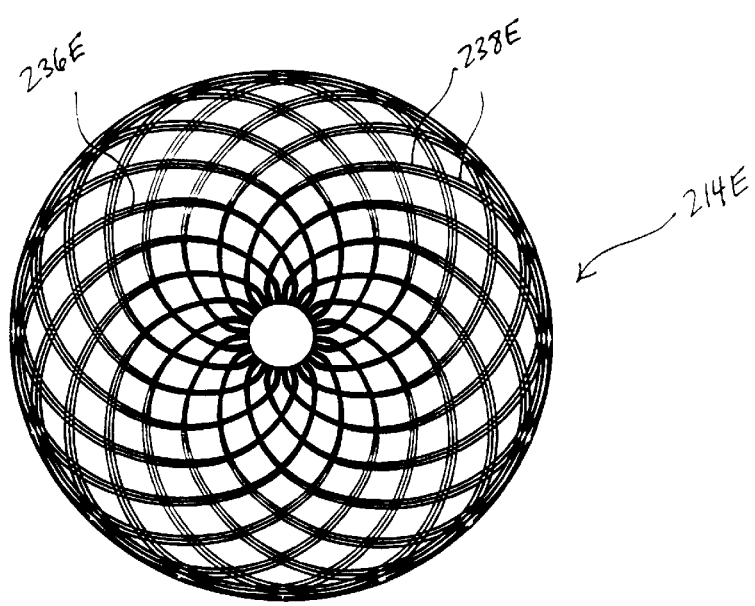
FIG. 41 is an end elevation view of the device shown in FIG. 40.

Each of the filaments 238E forming the braided elements 236E is preferably secured at opposite ends to the shaft 222E and the cannula 212E, as shown in FIGS. 40 and 41. The occluding member 214E assumes a generally bell-shaped configuration when expanded. The occluding member 214D has a fluid-impervious material 250E which substantially (and preferably completely) prevents flow around the member, with blood being delivered through the lumen of shaft 222E as in the above embodiments. The material 250E may be any suitable material such as silicone and may be integrally formed with the occluding member 214D, for example, by dipping the member in silicone, or, alternatively, it may be a separate sheath of such material secured to the member. It will be appreciated that the occluding member may take various shapes. Similarly, it will be understood that the occluding members in the previous embodiments could be formed to exhibit a bell (or other) shape when expanded.

Figure 42:
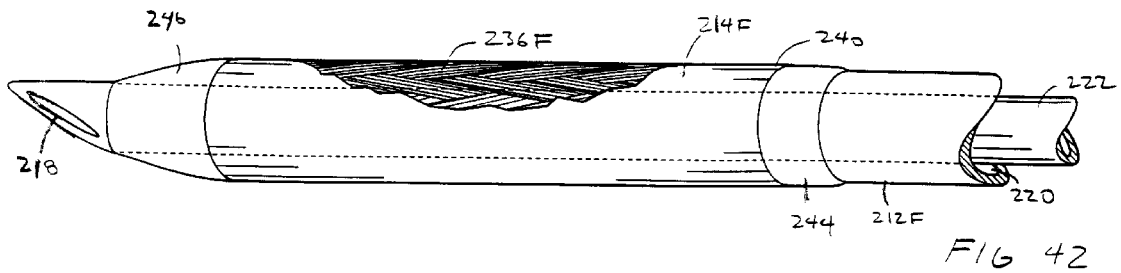
FIG. 42 is a side, partial cut-away view of yet another device.
Figure 43:
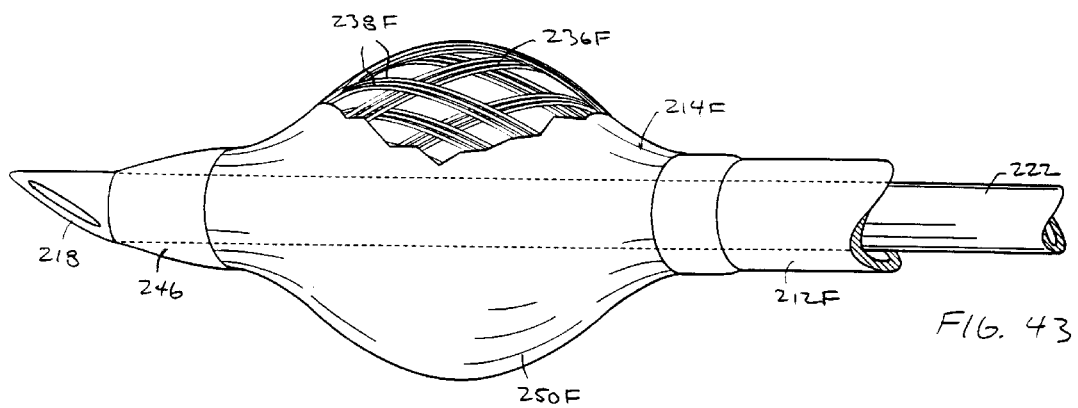
FIG. 43 is a side, parital cut-away view with the occluding member moving toward an expanded position.
Figure 44:
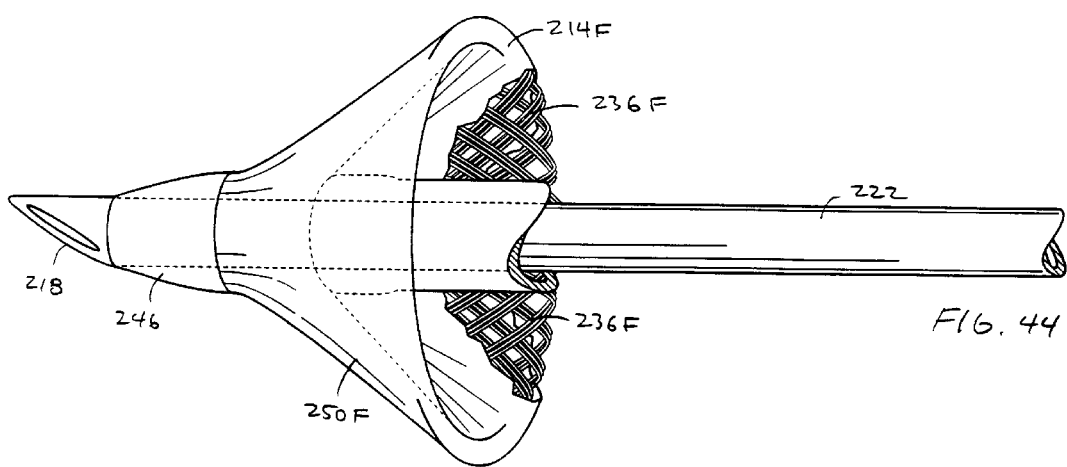
FIG. 44 is a side, partial cut-away view with the occluding member in the fully expanded position.

Referring to FIGS. 42–44 another cannula 212F and occluding member 214F wherein the occluding member is shown in three orientations. The cannula 212F is similar to the cannula 212 and like reference numbers refer to like structure. The occluding member 214F has a plurality of individual support elements which move relative to each other as the member is shifted between the collapsed and expanded orientations of FIGS. 42 and 44, respectively. In this embodiment, the individual support elements are in the form of braided elements 236F which overlap each other to form a mesh-like structure. Each of the braided elements 236F comprises a plurality of filaments 238F. Each of the braided elements 236 has a proximal end 240 and a distal end 242 which are secured, respectively, to a proximal section 244 and a distal section 246 of the cannula. These two sections 244, 246 are moved toward or away from each other to move the ends 240, 242 of the braided elements 236 toward or away from each other, thereby expanding or collapsing the occluding member 214. When in the expanded position, the occluding member 214F forms a bell-like structure having a generally frustoconical shape. A portion of the occluding member inverts when moving from the partially expanded shape of FIG. 43 to the fully expanded shape of FIG. 44. An advantage of this embodiment is that the occluding member 214F may be formed with a shorter length thereby providing more room for medical procedures near the occluding member 214F such as aortic valve procedures. The cannula 212F is preferably actuated with the same actuating mechanism as described above in connection with FIGS. 26–28.

Figure 45:
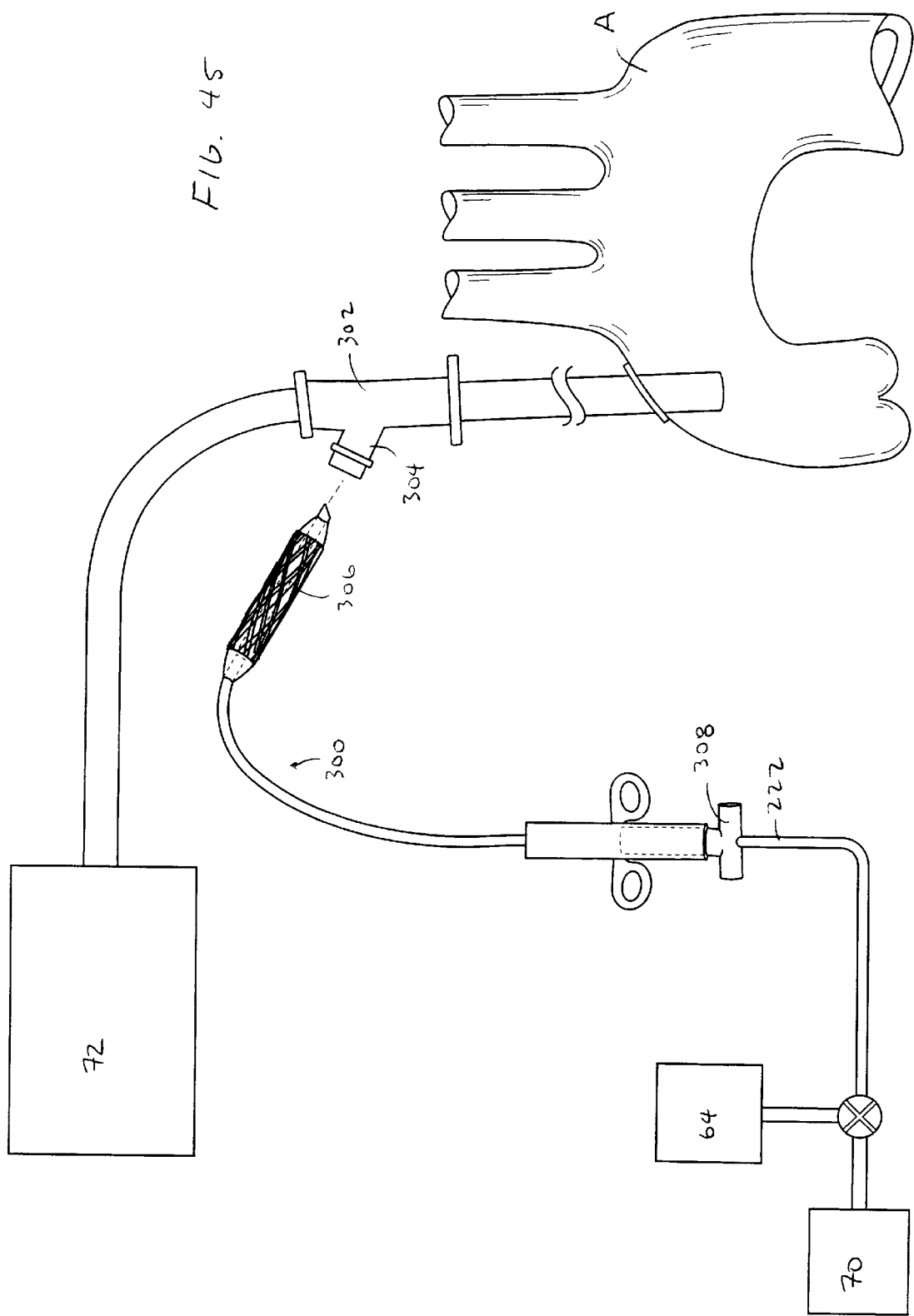
FIG. 45 is an elevation view of an aortic occlusion device and cannula constructed according to another embodiment of the invention, the device being shown in a collapsed orientation.
Figure 46:
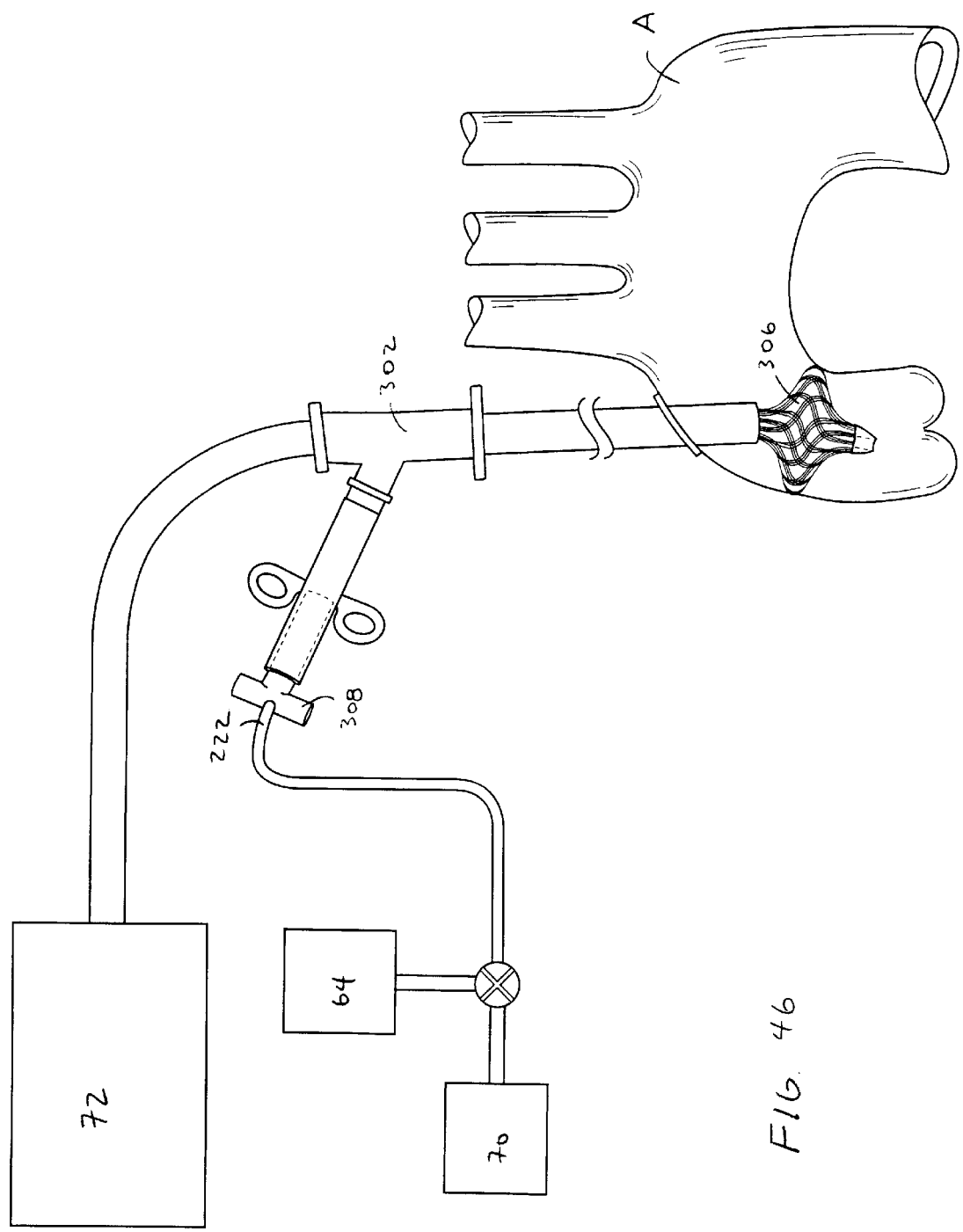
FIG. 46 is an elevation view of the aortic occlusion device of FIG. 44 shown positioned in the cannula in an expanded orientation.

As mentioned above, the occluding member, rather than being integrally formed with the cannula, may be a separate component that is used with a separate cannula. One possible embodiment according to this aspect of the invention is shown in FIGS. 45 and 46 and comprises an aortic occlusion device 300 and an arterial return cannula 302. The structure of the cannula 302 is essentially like that of the cannula 212 described above and includes an arm 304 configured to receive the occlusion device 300. The arm 304 has a hemostasis valve for receiving the aortic occlusion device 300. The device 300 comprises an occluding member 306 which preferably comprises an expandable braided structure as described above, the device including an actuator 308 which functions as in the previous embodiments. It should be appreciated that the occluding members in any of the previous embodiments may be used as a separate component in the manner shown in FIGS. 45 and 46.

The occluding device 300 is introduced into the cannula 302 with the occluding member 306 in a collapsed position (FIG. 45). Once positioned in the aorta, the actuator is used to expand the occluding member 306 to the position of FIG. 46 so as to substantially prevent blood flow around the member 306. Blood is infused into the patient through the cannula 302 from the source of oxygenated blood 72. The occluding device 300 has the shaft 222 through which cardioplegic fluid may be introduced from the source of cardioplegic fluid 64 or fluid vented from the ascending aorta with the vacuum source 70.

The invention of the embodiments of FIGS. 20–46 may be used in the same manner as described above, for example, as shown in FIGS. 12 and 17. The site at which the device is introduced into the patient's body may vary depending on the particular procedure being carried out and the surgeon's preference. Depending on the application, it may be desirable to place the device from the right or left side of the patient's body, and it also may be easier to carry out the procedure from a particular intercostal space, such as the $1^{st}$ or $2^{nd}$ intercostal space on the left side of the chest, or the $3^{rd}$ intercostal space in the right side of the chest.

Many variations and modifications of the invention disclosed herein will be readily apparent to persons skilled in the art. As such, it should be understood that the foregoing detailed description of preferred embodiments is made for purposes of setting forth a clear and complete disclosure, and is not intended to limit the scope of the invention which is defined by the claims which follow.

What is claimed is:

1. A device for occluding a patient's aorta, the device comprising:

a cannula having a lumen extending through at least a portion of the cannula;

a source of oxygenated blood coupled to the lumen which provides bypass support for the patient;

an occluding member provided on the cannula and movable between a collapsed orientation and an expanded orientation, the occluding member being sized and configured to occlude a patient's aorta when in said expanded orientation;

wherein the occluding member comprises a non-inflatable structure which moves mechanically from one of said collapsed and expanded orientations to the other of said orientations, the non-inflatable structure having an exterior that is at least substantially impervious to fluid to prevent fluid flow through a patient's aorta when the occluding member is positioned in the aorta in said expanded orientation, the occluding member being generally cylindrically-shaped when in said collapsed orientation and generally bell-shaped when in said expanded orientation;

wherein the non-inflatable structure includes a plurality of individual support elements which move relative to each other as the occluding member moves between said collapsed and expanded orientations; and an actuator for moving the occluding member from one of said collapsed and expanded orientations to the other of said orientations;

wherein substantially the entire occluding member is disposed inside the lumen of the cannula when the occluding member is in said collapsed orientation, and substantially the entire occluding member is disposed outside of the lumen of the cannula when the occluding member is in said expanded orientation.

2. The device of claim 1, wherein the actuator comprises a shaft which is movable within the lumen of the cannula, and each of the individual support elements has a first portion secured to the cannula and a second portion secured to the shaft, whereby relative movement of the cannula and the shaft moves the occluding member between said collapsed and expanded orientations.

3. The device of claim 2, wherein the shaft is axially movable within the lumen of the cannula.

4. The device of claim 2, further comprising a handle including first and second relatively movable portions coupled, respectively, to the cannula and the shaft.

5. The device of claim 2, wherein an annular space is defined between the cannula and the shaft and blood may flow through the annular space into the patient's aorta.

6. The device of claim 2, wherein the shaft has a lumen that communicates a portion of the device located proximal to the occluding member with a portion of the device located distal to the occluding member, and blood may flow through the lumen of the shaft into the patient's aorta.

7. The device of claim 1, wherein the individual support elements are interwoven with each other to form an expandable braided structure.

8. The device of claim 7, wherein each of the individual support elements comprises a plurality of discreet filaments that are disposed generally parallel to each other.

9. The device of claim 7, wherein the individual support elements are coated with a fluid-impervious substance.

10. The device of claim 9, wherein the individual support elements are braided such that the exterior of the occluding member is substantially imperforate when the occluding member is in said collapsed orientation, and such that the exterior of the occluding member defines open areas when the occluding member is in said expanded orientation, the fluid impervious substance preventing fluid flow through the open areas when the occluding member is in said expanded orientation.

11. The device of claim 1, wherein the individual support elements have an integral coating of a fluid-impervious material.

12. The device of claim 1, wherein the fluid-impervious material is silicone.

13. The device of claim 1, wherein the occluding member is generally tubular and includes proximal and distal ends separated by a central portion, the cross-sectional dimensions of the proximal end, distal end and central portion being substantially equal when the occluding member is in said collapsed orientation, and the cross-sectional dimension of the central portion being greater than the cross-sectional dimensions of the proximal and distal ends when the occluding member is in said expanded orientation.

14. The device of claim 1, wherein the individual support elements overlap each other and are movable relative to each other in a circumferential direction with respect to a longitudinal axis of the cannula.

15. The device of claim 1, wherein the individual support elements are flexible struts which are straight when the occluding member is in said collapsed orientation and bowed when the occluding member is in said expanded orientation.

16. The device of claim 1, wherein the individual support elements are helical coils which are closer together when the occluding member is in said collapsed orientation than in said expanded orientation.

17. The device of claim 1, wherein the individual support elements are flexible cross-members secured to each other so as to define adjacent openings, wherein the cross-members flex as the occluding member moves between said collapsed and expanded orientations.

18. The device of claim 1, wherein the individual support elements are covered by a sheath of a fluid-impervious material.

19. The device of claim 18, wherein the fluid-impervious material is silicone.

* * * * *